(12) United States Patent
Britton et al.

(10) Patent No.: US 12,006,528 B2
(45) Date of Patent: Jun. 11, 2024

(54) CELL-FREE PRODUCTION OF GERANYL PYROPHOSPHATE FROM GLYCEROL IN A CELL-FREE MANUFACTURING SYSTEM

(71) Applicant: Debut Biotechnology, Inc., San Diego, CA (US)

(72) Inventors: Joshua Britton, San Diego, CA (US); Nicholas Brideau, San Diego, CA (US)

(73) Assignee: DEBUT BIOTECHNOLOGY, INC., San Diego, CA (US)

( * ) Notice: Subject to any disclaimer, the term of this patent is extended or adjusted under 35 U.S.C. 154(b) by 0 days.

(21) Appl. No.: 17/554,537

(22) Filed: Dec. 17, 2021

(65) Prior Publication Data

US 2022/0195469 A1 Jun. 23, 2022

Related U.S. Application Data

(60) Provisional application No. 63/127,836, filed on Dec. 18, 2020, provisional application No. 63/127,758, filed on Dec. 18, 2020.

(51) Int. Cl.
*C12P 9/00* (2006.01)
*B01L 3/00* (2006.01)
*C12P 7/42* (2006.01)

(52) U.S. Cl.
CPC .......... *C12P 9/00* (2013.01); *B01L 3/00* (2013.01); *C12P 7/42* (2013.01); *B01L 2200/028* (2013.01); *B01L 2200/0631* (2013.01); *B01L 2200/0689* (2013.01); *B01L 2200/146* (2013.01); *B01L 2200/147* (2013.01); *B01L 2300/048* (2013.01); *B01L 2300/0663* (2013.01); *B01L 2300/0832* (2013.01); *B01L 2300/163* (2013.01); *B01L 2300/1894* (2013.01)

(58) Field of Classification Search
CPC ...... C12P 9/00; C12P 7/42; C12P 7/40; C12P 19/32; B01L 3/00; B01L 2200/028; B01L 2200/0631; B01L 2200/0689; B01L 2200/146; B01L 2200/147; B01L 2300/048; B01L 2300/0832; B01L 2300/163; B01L 2300/1894; B01J 19/004
See application file for complete search history.

(56) References Cited

U.S. PATENT DOCUMENTS

| | | |
|---|---|---|
| 6,524,842 B1 | 2/2003 | Vainberg et al. |
| 2010/0081182 A1 | 4/2010 | Paul et al. |
| 2010/0129886 A1 | 5/2010 | Anthony et al. |
| 2014/0273144 A1 | 9/2014 | Hawkins et al. |
| 2017/0218405 A1 | 8/2017 | Maggio-Hall et al. |
| 2017/0226497 A1 | 8/2017 | Kelly et al. |
| 2018/0252713 A1 | 9/2018 | Weiss et al. |
| 2020/0080115 A1 | 3/2020 | Clark et al. |
| 2020/0165558 A1 | 5/2020 | Shevitz |
| 2020/0255881 A1 | 8/2020 | Watkins et al. |
| 2022/0177940 A1* | 6/2022 | Mahour ................... C12P 19/00 |
| 2022/0193655 A1* | 6/2022 | Britton .................... B01J 19/004 |
| 2022/0403346 A1* | 12/2022 | Mikheev ................. C12N 15/10 |

FOREIGN PATENT DOCUMENTS

EP 3901256 A1 10/2021

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Valliere AM., A Synthetic Biochemistry Platform for the Enzymatic Synthesis of Cannabinoids and Other Prenylated Natural Products. Ph.D., Thesis, UCLA, pp. 1-121, publication date 2019. (Year: 2019).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Chuck, 2014, Liquid transport fuels from microbial yeasts—current and future perspectives, Biofuels, 5(3):293-311.

(Continued)

*Primary Examiner* — Ganapathirama Raghu
(74) *Attorney, Agent, or Firm* — Brown Rudnick LLP; Adam M. Schoen

(57) ABSTRACT

Geranyl pyrophosphate (GPP) is a key intermediate molecule in the bioproduction of thousands of natural products. Currently, natural products are either cultivated from plants, synthesized via complex chemical synthesis strategies, or through cell-based factories also known as biofoundries. However, in order to replicate the process in a cell free environment, numerous enzymes and cofactors must be utilized making this approach costly and unviable. In order to make this process viable, a new approach was needed that uses fewer enzymes and co-factors. As described herein, the present invention demonstrates that it is possible to create GPP from glycerol through a short and concise biosynthetic pathway outside of the cell.

15 Claims, 2 Drawing Sheets

Specification includes a Sequence Listing.

(56) References Cited

OTHER PUBLICATIONS

Clomburg, 2019, The isoprenoid alcohol pathway, a synthetic route for isoprenoid biosynthesis, PNAS, 116(26):12810-12815.
Degenhardt, 2018, Evaluation of C-prenylating enzymes for the heterologous biosynthesis of cannabigerolic acid, Technical Univeristy Dortmund, 180 pages.
Dudley, 2017, Cell-free Biosynthess of Isoprenoids using *Escherichia coli* Crude Lysates, Nothwestern University, 280 pages.
Gao, 2014, An artificial enzymatic reaction cascade for a cell-free bio-system based on glycerol, Green Chemistry, 2(17):804-807.
International Search Report and Written Opinion issued in International Application No. PCT/US2021/063992, dated Mar. 18, 2022, 9 pages.
International Search Report and Written Opinion issued in International Application No. PCT/US2021/064034, dated Mar. 10, 2022, 11 pages.
International Search Report and Written Opinion issued in International Application No. PCT/US2021/064049, dated Mar. 9, 2022, 8 pages.
Sutiono, 2020, Enabling the Direct Enzymatic Dehydration of D-Glycerate to Pyruvate as the Key Step in Synthetic Enzyme Cascades Used in the Cell-Free Production of Fine Chemicals, ACS Catal, 10(5):3110-3118.
Valliere, 2019, A cell-free platform for the prenylation of natural products and application to cannabinoid production. Nature Communications, 10(565), 9 pages.

* cited by examiner

CELL-FREE PRODUCTION OF GERANYL PYROPHOSPHATE FROM GLYCEROL IN A CELL-FREE MANUFACTURING SYSTEM

CROSS-REFERENCES TO RELATED APPLICATIONS

This application is a non-provisional and claims benefit of U.S. Provisional Application No. 63/127,836 filed Dec. 18, 2020 and of U.S. Provisional Application No. 63/127,758 filed Dec. 18, 2020, the specification of which is incorporated herein in their entirety by reference.

REFERENCE TO A SEQUENCE LISTING

Applicant asserts that the paper copy of the Sequence Listing is identical to the Sequence Listing in computer readable form found on the accompanying computer file, entitled DEBUT_20_03_NP_Sequence_Listing_ST25. The content of the sequence listing is incorporated herein by reference in its entirety.

FIELD OF THE INVENTION

The present invention features a method of producing geranyl pyrophosphate (GPP) from glycerol, in particular, the present invention features a cell-free production method.

BACKGROUND OF THE INVENTION

Geranyl pyrophosphate (GPP) is a key intermediate molecule in the bioproduction of thousands of natural products. Here, a natural product is a molecule formed through multi-step enzyme-pathways in organisms such as plants, animals, and bacteria. Currently, natural products are either cultivated from plants, synthesized via complex chemical synthesis strategies, or through cell-based factories also known as bio-foundries.

Previously, Valliere et. al. 2019 manufactured GPP in a cell free environment using glucose as a starting material. This complete replica of a natural enzyme system uses 22 enzymes and requires 40 cofactor equivalents including 12 adenosine triphosphate (ATP), 12 adenosine diphosphate (ADP), four nicotinamide adenine dinucleotide phosphate (NADP⁺), two nicotinamide adenine dinucleotides (NAD⁺), six acetyl-coenzyme A (CoA), and four nicotinamide adenine dinucleotide phosphate (NADPH). The number of cofactors required by the process described in the current literature means that this approach will always be costly and unviable (FIG. 1B). In order to make this process viable, a new approach is needed that uses fewer enzymes and cofactors and improves reliability. As described herein, the present invention demonstrates that it is possible to create GPP through a short and concise biosynthetic pathway outside of the cell; known as cell-free biosynthesis.

BRIEF SUMMARY OF THE INVENTION

It is an objective of the present invention to provide a cell-free method that allows for the production of producing geranyl pyrophosphate (GPP) and additional secondary metabolites starting from glycerol via a cell-free biosynthesis platform, as specified in the independent claims. Embodiments of the invention are given in the dependent claims. Embodiments of the present invention can be freely combined with each other if they are not mutually exclusive.

Manufacturing natural products via cultivation, chemical synthesis, or in the cell suffers from many problems that limit the commercial viability of high-value chemical production. First, cultivation is often economically unfeasible, requires a vast amount of land/energy/water and the plant is only capable of producing the high-value material in low amounts. Next, chemical synthesis requires extensive, elaborate, expensive, toxic, and inefficient multi-step chemical reactions to produce natural products that often are too complex to make in the laboratory. Finally, bio-foundries (use of the whole cell) suffer from product toxicity, carbon flux redirection, diffusion problems through cell walls, and toxic byproduct generation. To avoid these above problems, cell-free manufacturing presents as a viable alternative.

In cell-free systems, the key components of the cell namely cofactors and enzymes are used in a chemical reaction without the cell. The same enzymes that are found in plants, animals, and bacteria are created in vivo (typically through protein overexpression in hosts such as bacteria), isolated via chromatography, and then added into a bioreactor with a substrate (starting material). The enzymes transform the substrate in the same way that occurs in plants, animals, and bacteria, but without the complexity of the organism. In this way, natural products can begin to be created without the plant, cell, or chemical synthesis.

The present invention creates an enzyme pathway that removes the glycolysis pathway (glucose to pyruvic acid) to allow a shorter, affordable, and simpler process to convert glycerol into GPP (FIG. 1A). The presently claimed process uses 12 enzymatic steps and eliminates 24 cofactor equivalents and ten enzymes (FIG. 1B). Additionally, enzyme immobilization was used to improve conversion to GPP by avoiding enzyme precipitation, inactivation, and the unreliability of the non-immobilized system. The present invention also provides evidence that demonstrates that without enzyme immobilization, enzyme precipitation and destruction of the enzyme pathway is observed. Finally, this process starts with glycerol and not glucose. Glycerol is an abundant natural material that is not used in the production of GPP; this invention allows this natural waste product to be utilized as a viable alternative to glucose.

In some embodiments, the present features a method of converting glycerol to geranyl pyrophosphate (GPP) and additional secondary metabolites. In some embodiments, the method comprises adding glycerol to a reaction mixture. In some embodiments, the method comprises adding a plurality of enzymes to the aforementioned reaction mixture. In some embodiments, the enzymes are selected from a group consisting of alditol oxidase (Aldo), dihydroxy-acid dehydratase (DHAD), pyruvate oxidase (PyOx), acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), and farnesyl-PP synthase S82F (FPPS). In some embodiments, the method comprises removing a supernatant from the aforementioned reaction mixture. In some embodiments, the method comprises isolating or producing GPP. In some embodiments, the enzymes may be added to the reaction mixture asynchronously. In other embodiments, the enzymes may be added to the reaction mixture simultaneously.

In other embodiments, the present invention features a method of converting glycerol to geranyl phosphate (GPP) and additional secondary metabolites. In some embodiments, the method comprises adding glycerol and alditol oxidase (Aldo) to a reaction mixture. In some embodiments, the method further comprises adding dihydroxy-acid dehydratase (DHAD) to the reaction mixture. In some embodiments, the method comprises removing a supernatant of the aforementioned reaction mixture and adding pyruvate oxidase (PyOx) to the supernatant of the reaction mixture. In some embodiments, the method comprises removing a supernatant of the aforementioned reaction mixture and at least two enzymes selected from a group consisting of acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), and farnesyl-PP synthase S82F (FPPS) to the supernatant of the reaction mixture. In some embodiments, the method comprises removing a supernatant from the aforementioned reaction mixture and producing GPP. In some embodiments, the enzymes may be added to the reaction mixture asynchronously. In other embodiments, the enzymes may be added to the reaction mixture simultaneously.

One of the unique and inventive technical features of the present invention is the use of a cell-free system for the production of geranyl pyrophosphate (GPP) and additional secondary metabolites starting from glycerol. Without wishing to limit the invention to any theory or mechanism, it is believed that the technical feature of the present invention advantageously provides for higher reaction concentrations, no cell-wall to battle for product and substrate diffusion, no competition in the cell for carbon flux and byproduct formation, no cell death due to the formation of toxic compounds (there is no cell), and increased flexibility as a platform solution for creating a large number of compounds compared to cells having to be re-programmed every time. In this approach, one may simply change an enzyme in the pathway to create a new chemical entity.

Furthermore, the prior references teach away from the present invention. For example, Valliere et. al. 2019 used a more complex cell-free system to generate GPP as an intermediate in the production of cannabidiol (CBD) from glucose. The pathway of the present invention eliminates 60% of the expensive cofactors, ten enzymes, and an elaborate purge valve and uses an alternative starting material. While the present invention shares 10 enzymes with the Valliere et. al. approach, the present invention has significantly improved the enzyme activity, longevity and reliability by immobilizing and optimizing all 10 enzymes. Of note, Valliere et. al. contains data demonstrating enzyme precipitation following incubation of all enzymes in a reaction mixture. Precipitation of these enzymes was also seen when repeating the work in as little as 16 hours after being combined in a reaction mixture, severely limiting the previous work. The key success was the immobilization of each of the 12 enzymes to allow the enzymes to remain active in reaction mixtures for extended periods of time via eliminating precipitation.

Furthermore, the inventive technical features of the present invention contributed to a surprising result. The first module in the pathway of the present invention converts glycerol to pyruvic acid by combining the activity of alditol oxidase (ALDO) and dihydroxy acid dehydratase (DHAD) as reported in Gao et. al. 2015. Surprisingly, the present invention had to make several modifications to this published work in order to successfully generate pyruvic acid from glycerol. First, a maltose binding protein was added to the N-terminus of *Streptomyces* ALDO to aid in solubility and stability while maintaining activity of the enzyme (SEQ ID NO: 1). Second, it was found that MBP-ALDO required oxygenation for optimal activity. Third, *Sulfolobus solfataricus* DHAD as reported in Gao et. al. 2015 was not functional. Many DHAD orthologs were screened and *Thermosynechococcus vulcanus* DHAD (SEQ ID NO: 2) was found to be the most active. Fourth, it was found that DHAD required deoxygenation and a very specific pH range for optimal activity.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Figure 1A:
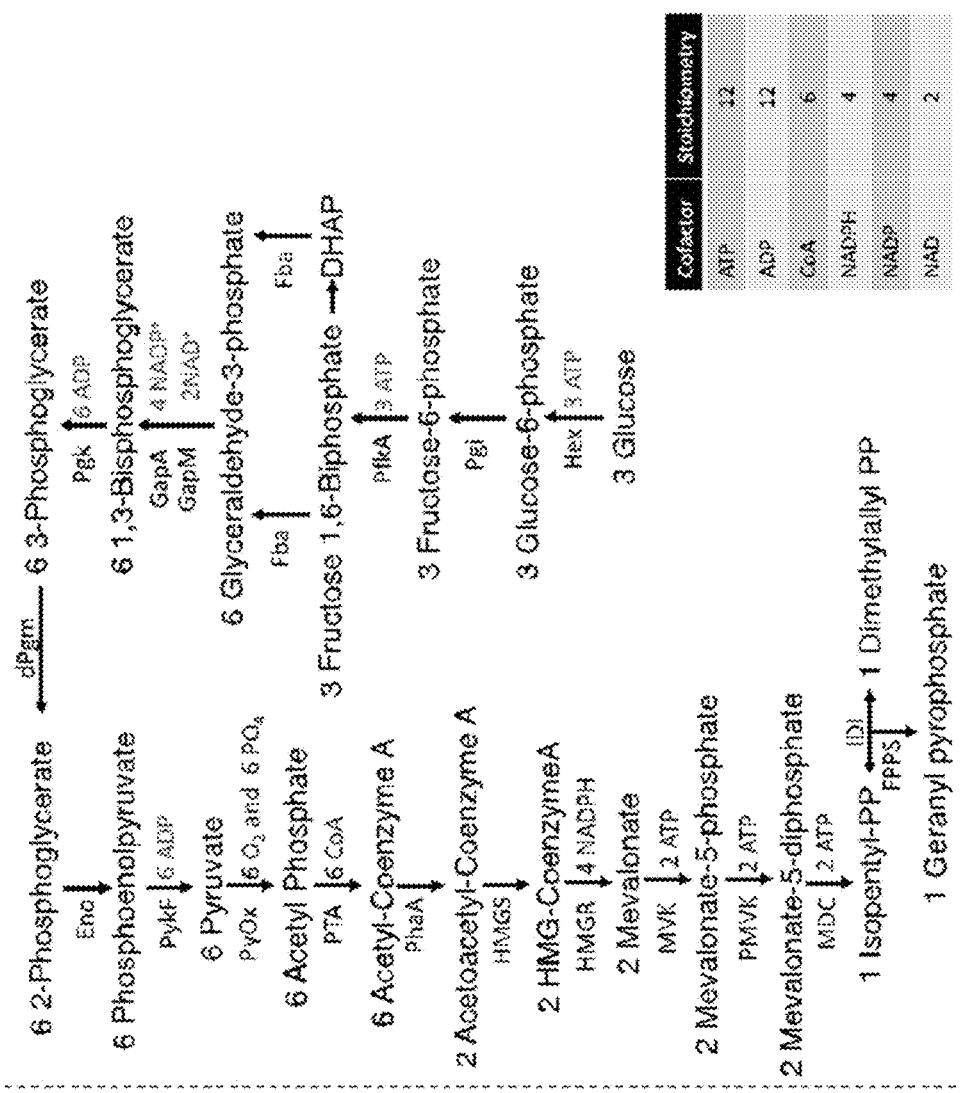
FIGS. 1A and 1B show the pathway used for the production of geranyl pyrophosphate (GPP), (left, FIG. 1A) vs. previous attempts to GPP from glucose (right, FIG. 1B). As shown the pathway on the left (FIG. 1A) has 70% fewer co-factors and 10 fewer enzymes.

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising.

As used herein, "reaction solution" may refer to all components necessary for enzyme-based chemical transformation. This is typically, but not limited to, buffering agent, salts, cofactor, and substrate (i.e., starting material).

As used herein, "reaction mixture" may refer to all components from the "reaction solution" plus the enzyme(s) and/or products from the reaction. In some embodiments, the "reaction mixture" may refer to just the reaction solution without any enzymes or reaction products.

In some embodiments, "reaction solution" and "reaction mixture" may be used interchangeably.

As used herein, "buffering agents" may refer to chemicals added to water-based solutions that resist changes in pH by the action of acid-base conjugate components.

As used herein, "supernatant" may refer to the soluble liquid fraction of a sample.

As used herein, "batch reactions" may refer to a chemical or biochemical reaction performed in a closed system such as a fermenter or typical reaction flask.

As used herein, "cofactors" may refer to a non-protein chemical compound that may bind to a protein and assist with a biological chemical reaction. Co-factors may be metal ions, organic compounds, or other chemicals. Non-limiting examples of cofactors may include but are not limited to ATP and NADPH.

As used herein, "cofactor recycling" may refer to regeneration of functional cofactor capable of participating in enzyme-catalyzed reactions. A non-limiting example of this regeneration is a separate reaction acting on the altered cofactor produced by a primary enzymatic reaction, such as the enzymatic conversion of ADP back to ATP.

Referring now to FIGS. 1A, 1B, 2A, and 2B, the present invention features a method of producing geranyl pyrophosphate (GPP) and additionally secondary metabolites from glycerol.

The present features a method of converting glycerol to geranyl pyrophosphate (GPP) and additional secondary metabolites. In some embodiments, the method comprises adding glycerol to a reaction mixture. In some embodiments, the method comprises adding a plurality of enzymes to the aforementioned reaction mixture. In some embodiments, the enzymes are selected from a group consisting of alditol oxidase (Aldo), dihydroxy-acid dehydratase (DHAD), pyruvate oxidase (PyOx), acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), and farnesyl-PP synthase S82F (FPPS). In some embodiments, the method comprises removing a supernatant from the aforementioned reaction mixture. In some embodiments, the method comprises isolating or producing GPP.

The present invention may also feature a method of converting glycerol to geranyl phosphate (GPP) and additional secondary metabolites. In some embodiments, the method comprises adding glycerol and alditol oxidase (Aldo) to a reaction mixture. In some embodiments, the method further comprises adding dihydroxy-acid dehydratase (DHAD) to the reaction mixture. In some embodiments, the method comprises removing a supernatant of the aforementioned reaction mixture and adding pyruvate oxidase (PyOx) to the supernatant of the reaction mixture. In some embodiments, the method comprises removing a supernatant of the aforementioned reaction mixture and at least two enzymes selected from a group consisting of acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), and farnesyl-PP synthase S82F (FPPS) to the supernatant of the reaction mixture. In some embodiments, the method comprises removing the supernatant from the aforementioned reaction mixture and producing or isolating GPP.

In some embodiments, at least one enzyme is added to the reaction mixture. In some embodiments, at least two enzymes are added to the reaction mixture. In some embodiments, at least three enzymes are added to the reaction mixture. In some embodiments, at least four enzymes are added to the reaction mixture. In some embodiments, at least five enzymes are added to the reaction mixture. In some embodiments, at least six enzymes are added to the reaction mixture. In some embodiments, at least seven enzymes are added to the reaction mixture. In some embodiments, at least eight enzymes are added to the reaction mixture. In some embodiments, at least nine enzymes are added to the reaction mixture. In some embodiments, at least ten enzymes are added to the reaction mixture. In some embodiments, at least eleven enzymes are added to the reaction mixture. In some embodiments, at least twelve enzymes are added to the reaction mixture.

In some embodiments, the enzymes may be added to the reaction mixture asynchronously. In other embodiments, the enzymes may be added to the reaction mixture simultaneously.

In some embodiments, the method further comprises adding a NphB enzyme before the final removal of the supernatant from the reaction mixture to convert GPP to cannabigerolic acid (CBGA). In some embodiments, CBGA is used to determine the amount of GPP produced in the above-mentioned method. In some embodiments, the production of CBGA is used as an analytical tool. In some embodiments, the production of CBGA from GPP by NphB is used as a detection method. In some embodiments, the production of CBGA by NphB is used to detect the amount of GPP. In some embodiments, the amount of CBGA produced from the conversion of GPP by the NphB enzyme is 1:1.

In some embodiments, the reaction mixtures described herein comprise cofactors. In some embodiments, the cofactors comprise adenosine triphosphate (ATP), nicotinamide adenine dinucleotide ($NAD^+$), nicotinamide adenine dinucleotide phosphate ($NADP^+$), or a combination thereof. In some embodiments, the methods described herein utilized cofactor recycling. In some embodiments, the cofactors are recycled. In some embodiments, the method further comprises adding glucose dehydrogenase (GDH), and polyphosphate kinase 2 (PPK2) to the reaction mixture. In some embodiments, glucose dehydrogenase (GDH), and polyphosphate kinase 2 (PPK2) are added to the reaction mixture to recycle the co-factors.

In some embodiments, the temperature of the reaction may range from about 22° C. to about 50° C. In some embodiments, the temperature of the reaction is about 20° C. In some embodiments, the temperature of the reaction is about 25° C. In some embodiments, the temperature of the reaction is about 30° C. In some embodiments, the temperature of the reaction is about 35° C. In some embodiments, the temperature of the reaction is about 40° C. In some embodiments, the temperature of the reaction is about 45° C. In some embodiments, the temperature of the reaction is about 50° C. In some embodiments, the temperature of the reaction is about 55° C.

In some embodiments, the pH of the reaction may range from about 6.5 to about 9.0. In some embodiments, the pH of the reaction is about 5.0. In some embodiments, the pH of the reaction is about 5.5. In some embodiments, the pH of the reaction is about 6.0. In some embodiments, the pH of the reaction is about 6.5. In some embodiments, the pH of the reaction is about 7.0. In some embodiments, the pH of the reaction is about 8.5. In some embodiments, the pH of the reaction is about 9.0. In some embodiments, the pH of the reaction is about 9.5. In some embodiments, the pH of the reaction is about 10.0.

In some embodiments, the time to run the reaction may range from about 2 hours to about 32 hours. In some embodiments, the time to run the reaction is about 0.5 hour. In some embodiments, the time to run the reaction is about 1 hour. In some embodiments, the time to run the reaction is about 2 hours. In some embodiments, the time to run the reaction is about 5 hours. In some embodiments, the time to run the reaction is about 10 hours. In some embodiments, the time to run the reaction is about 15 hours. In some embodiments, the time to run the reaction is about 20 hours. In some embodiments, the time to run the reaction is about 25 hours. In some embodiments, the time to run the reaction is about 30 hours. In some embodiments, the time to run the reaction is about 35 hours. In some embodiments, the time to run the reaction is about 40 hours. In some embodiments, the time to run the reaction is about 45 hours. In some embodiments, the time to run the reaction is greater than 45 hours.

In some embodiments, the enzymes are immobilized. In some embodiments, immobilized enzymes are immobilized onto solid supports. Non-limiting examples of solid supports may include but are not limited to epoxy methacrylate, amino $C_6$ methacrylate, or microporous polymethacrylate. In further embodiments, various surface chemistries may be used for linking the immobilized enzyme to a solid surface, including but not limited to covalent, adsorption, ionic, affinity, encapsulation, or entrapment. In other embodiments, the enzymes are non-immobilized.

In some embodiments, one or more of the enzymes are immobilized. In other embodiments, all the enzymes are immobilized. In some embodiments, one or more of the enzymes are non-immobilized. In other embodiments, all the enzymes are non-immobilized. In some embodiments, the plurality of enzymes are immobilized. In other embodiments, the plurality of enzymes are non-immobilized.

In some embodiments, various reaction conditions may be altered to ensure functional enzymes, including but not limited to reaction time, oxygenation/deoxygenation, pH, buffering agents, and reaction temperature.

In some embodiments, the methods described herein teaches away from previously described methods because the presently claimed methods utilized less enzymes and co-factors to produce GPP. In certain embodiments, methods described herein do not use 24 cofactor equivalents used by Valliere et al., (or 60% of cofactors). In certain embodiments, only ten of the enzymes taught by Valliere et al. are used in the presently claimed method.

Example

The following is a non-limiting example of the present invention. It is to be understood that said example is not intended to limit the present invention in any way. Equivalents or substitutes are within the scope of the present invention.

Enzyme Expression and Purification: All genes were synthesized and cloned into expression plasmids and then transformed into *E. coli* cells for expression. Cells were grown in TB media supplemented with 50 µg/mL kanamycin sulfate at 37° C. and 200 rpm until $A_{600}$=0.6. Cells were cooled to 18° C., expression was induced and grown for an additional 18 h. Cell pellets were collected by centrifugation, frozen, and then resuspended in a 5 mL lysis buffer (50 mM Tris pH 8.0, 300 mM NaCl, 5% glycerol, 1 mM PMSF) per gram of cell paste. Cell lysates were prepared by sonication and cellular debris was removed by centrifugation. Clarified lysate was loaded onto GE XK series columns containing IMAC-Nickel resin. Proteins were eluted using a 15CV gradient from buffer A (50 mM Tris pH 8.0, 300 mM NaCl, 10% glycerol) into 70% buffer B (2 M imidazole, 50 mM Tris pH 8.0, 300 mM NaCl, 10% glycerol). Fractions containing proteins of interest were pooled and transitioned into buffer A (above) with a GE HiPrep 26/10 desalting column, with the exception of MBP-Aldo, which was stored in 50 mM Tris pH 8.0, 500 mM NaCl, 0.1% Triton X-100.

1.0 Production of GPP with the non-immobilized cell-free pathway: As described herein, the pathway first converts glycerol to glyceric acid using alditol oxidase (Aldo, EC 1.1.3.41) before subsequent conversion into pyruvic acid using dihydroxy-acid dehydratase (DHAD, EC 4.2.1.9, FIG. 1A). While the first two enzymes have been documented, several significant advancements were required to make this pathway functional, as the previously reported work could not be replicated.

To ensure functional enzymes, specific reaction conditions including timed reaction oxygenation, de-oxygenation, pH changes, specific buffers, and reaction temperature had to be found. First, the reported Aldo is unstable and inactive. To overcome this, a modified Aldo was created housing a fusion maltose-binding protein (MBP) tag to improve solubility and stability in solution (SEQ ID 1). The MBP-fused Aldo converted glycerol into glyceric acid (100%, 1.75 g/L). Second, the published reaction with *Sulfolobus solfataricus* DHAD was also not reproducible. To overcome this, many DHAD enzyme orthologs were screened; and it was found that DHAD from *Thermosynechococcus vulcanus* converted 100% of glyceric acid to pyruvic acid (1.32 g/L).

With these new enzymes, a one-pot reaction containing both Aldo (11 µM) and DHAD (16 µM) converted glycerol into pyruvic acid (100% conversion, yield 1.23 g/L). Compared to previous work starting from glucose, the present improved system afforded 14 mM of pyruvic acid in 24 hours, without the use of cofactors and nine fewer enzymes providing a significant improvement. It should also be noted that previous attempts from glucose require many additional enzymes, cofactors, and reaction manufacturing complications such as protein precipitation. Removing these constraints allows a commercially viable approach to GPP from an inexpensive carbon source.

Figure 1B:
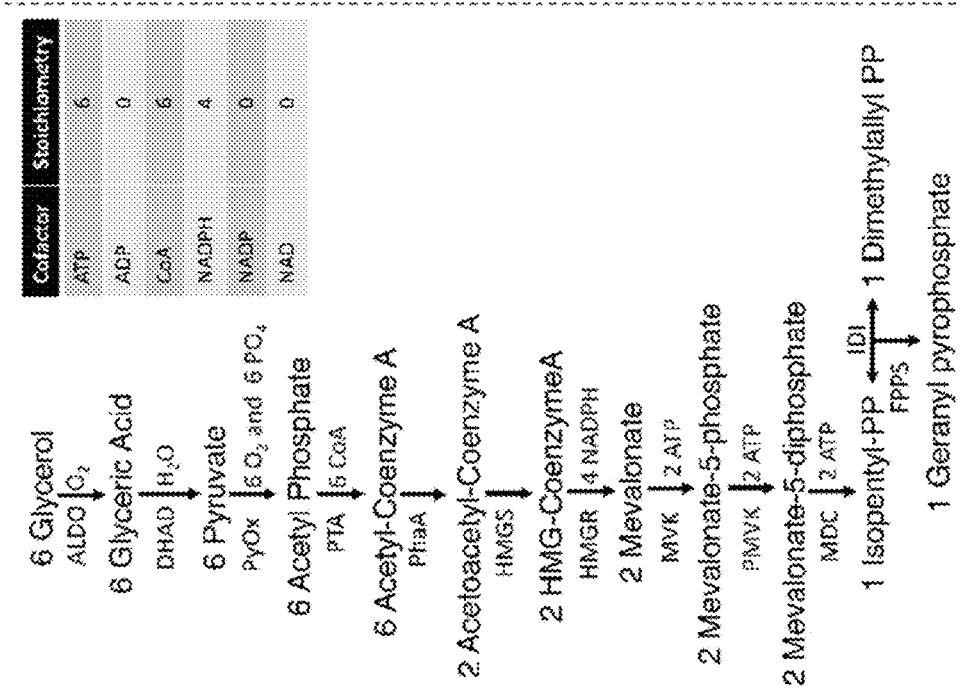

After optimization of Aldo and DHAD, the remaining enzymes in the pathway that convert pyruvic acid into geranyl pyrophosphate had to be created and optimized (GPP, FIGS. 1A and 1B). After optimization of each individual enzyme, GPP was afforded (43 mg/L in 120 hours). This result validated the shorter improved pathway with far fewer cofactors for GPP manufacturing, however, protein precipitation was observed after several days meaning that this approach would not be suitable for commercial production. To overcome this limitation, each protein in the pathway was immobilized onto solid supports to ensure the protein remained active and operational; this required extensive optimization and understanding to create each individual enzyme-solid support complex.

2.0 Protein Immobilization and Optimization: To increase stability, longevity, and catalysis, each purified enzyme in the pathway was immobilized onto solid supports. Different commercial support materials were routinely screened for product and substrate retention, enzyme retention, and activity of the immobilized enzyme. The support collection comprised of various surface chemistries for the following types of linkage: covalent, adsorption, ionic, affinity, encapsulation, and entrapment. Typically, 50 mg of resin was mixed with 4.0 mg of an enzyme in a desalting buffer 16-24 h at room temperature. The amount of immobilized enzyme was quantified by measuring protein concentration in solution before and after immobilization by either BCA or Bradford assay. All immobilized enzymes were screened for optimal values for resin type, substrate concentration (5 mM-250 mM), pH (5.0-9.0), temperature (20-50° C.), buffering agent (Tris, HEPES, $PO_4$), and time (1 h-36 h). Optimal reaction conditions and results for each enzyme are as follows (Table 1A).

TABLE 1A

Conditions found for the immobilized enzymes used in the GPP biomanufacturing route (FIG. 1A).

| | Reaction Conditions Screened | | | |
|---|---|---|---|---|
| Enzyme Name | Temp (° C.) | pH | Time (h) | Yield (%) |
| MBP-Aldo (Aldo) | 37 | 9.0 | 21 | 98 |
| Dihydroxy Acid Dehydratase (DHAD) | 45 | 8.0 | 16 | 32 |
| Pyruvate Oxidase (PyOx) | 37 | 6.5 | 16 | 91 |
| Acetyl-phosphate transferase (PTA) | 32 | 8.0 | 8 | 60 |
| Acetyl-CoA acetyltransferase (PhaA) | 32 | 8.0 | 8 | 44 |
| HMG-CoA Synthase A110G (HMGS) | 32 | 7.5 | 2 | 54 |
| HMG-CoA Reductase (HMGR) | 37 | 7.0 | 2 | 98 |
| Mevalonate Kinase (MVK) | 37 | 8.0 | — | 87 |
| Phosphomevalonate Kinase (PMVK) | 37 | 8.0 | 32 | 96 |
| Diphosphomevalonate Kinase (MDC) | 37 | 8.0 | 16 | 94 |
| Isopentyl-PP Isomerase (IDI) | 22 | 8.0 | 2 | 28 |
| Farnesyl-PP synthase S82F (FPPS) | 25 | 8.3 | 4 | 81 |
| Prenyl transferase (NphB) | 50 | 8.0 | 6 | 16 |

The percent yields in the foregoing table are presented for illustrative purposes. In some embodiments, each step of the GPP biomanufacturing process may have a percent yield of up to 99%, up to 99.5%, up to 99.9% or up to 100%. In some embodiments, the percent yields in each step of the GPP biomanufacturing process may have values within the ranges in the following table (Table 1B).

TABLE 1B

Exemplary ranges for the immobilized enzymes that may be used in the GPP biomanufacturing route (FIG. 1A).

| | Exemplary Reaction Conditions | | | |
|---|---|---|---|---|
| Enzyme Name | Approximate Temp (° C.) | Approximate pH | Approximate Time (h) | Yield (%) |
| MBP-Aldo (Aldo) | 37 | 9 | 21 | 98-100% |
| Dihydroxy Acid Dehydratase (DHAD) | 45 | 8.0 | 16 | 32-100% |
| Pyruvate Oxidase (PyOx) | 37 | 6.5 | 16 | 91-100% |
| Acetyl-phosphate transferase (PTA) | 32 | 8.0 | 8 | 60-100% |
| Acetyl-CoA acetyltransferase (PhaA) | 32 | 8.0 | 8 | 44-100% |
| HMG-CoA Synthase A110G (HMGS) | 32 | 7.5 | 2 | 54-100% |
| HMG-CoA Reductase (HMGR) | 37 | 7.0 | 2 | 98-100% |
| Mevalonate Kinase (MVK) | 37 | 8.0 | — | 87-100% |
| Phosphomevalonate Kinase (PMVK) | 37 | 8.0 | 32 | 96-100% |
| Diphosphomevalonate Kinase (MDC) | 37 | 8.0 | 16 | 94-100% |
| Isopentyl-PP Isomerase (IDI) | 22 | 8.0 | 2 | 28-100% |
| Farnesyl-PP synthase S82F (FPPS) | 25 | 8.3 | 4 | 81-100% |
| Prenyl transferase (NphB) | 50 | 8.0 | 6 | 16-100% |

2.1 Optimization of Alditol Oxidase (Aldo): MBP-Aldo was immobilized onto activated amino $C_6$ methacrylate resin. The immobilized enzyme was used to convert glycerol into glyceric acid. The reaction solution (50 mM Tris pH 9, 2.5 mM $MgCl_2$, 20 mM glycerol) was mixed with 50 μM immobilized enzyme at 37° C. for 21 hours. Immobilized MBP-Aldo converted 100% of 20 mM glycerol to yield 20 mM (1.75 g/L) glyceric acid. For sampling, the reaction mixture was analyzed through high-performance liquid chromatography (HPLC). The HPLC method was as follows: An Agilent 1200 HPLC was fitted with a 30 cm Aminex HPX-87H column equipped with a micro-guard cation H refill cartridge. The column was heated to 55° C. with the sample block being maintained at 25° C. For each sample, 1 μL was injected, and using a mobile phase comprised of 100% sulfuric acid (10 mM). The sample time was a total of 45 minutes with glyceric acid eluting at 17.2 mins and glycerol eluting at 21.0 minutes. A Refractive Index Detector (RID, Agilent) was used after a 2 h equilibration period produced a stable baseline.

2.2 Optimization of Dihydroxy Dehydratase (DHAD): DHAD was mixed with activated amino $C_6$ methacrylate resin and the immobilized enzyme was used to convert glyceric acid into pyruvic acid. The reaction solution (50 mM Tris pH 8.5, 2.5 mM $MgCl_2$, 20 mM glyceric acid) was mixed with 50 μM immobilized enzyme at 45° C. for 16 hours. Immobilized DHAD was able to convert 99% of 20 mM glyceric acid for a yield of 15 mM (1.32 g/L, 75%) pyruvic acid. For sampling, the reaction mixture was examined on an HPLC system to examine the amount of glycerol and glyceric acid. The HPLC method was as follows: An Agilent 1200 HPLC was fitted with a 30 cm Aminex HPX-87H column equipped with a micro-guard cation H refill cartridge. The column was heated to 55° C. with the sample block being maintained at 25° C. For each sample, 1 μL was injected and an isocratic gradient comprised of 100% sulfuric acid (10 mM) was used as the mobile phase. The sample time was a total of 45 minutes with pyruvic acid eluting at 16.0 minutes and glyceric acid eluting at 17.2 mins. A Refractive Index Detector (Agilent) was used after a 2 h equilibration period produced a stable baseline.

2.3 Optimization of Pyruvate Oxidase (PyOx): PyOx was mixed with activated amino $C_6$ methacrylate resin and the immobilized enzyme was used to convert pyruvic acid into acetyl phosphate. The reaction solution (10 mM Tris, 50 mM $KH_2PO_4$, 50 mM $K_2HPO_4$, pH 6.5, 5.0 mM $MgCl_2$, 100 mM NaCl, 20 mM pyruvic acid, 20 mM thiamine pyrophosphate) was mixed with 3.85 µM immobilized enzyme at 37° C. for 16 hours. Immobilized PyOx was able to convert 91% of 5 mM pyruvate for a yield of 4.55 mM (837 mg/L) acetyl phosphate. For sampling, the reaction fluid was examined on an HPLC system to examine the amount of pyruvate and acetyl phosphate. The HPLC method was as follows: An Agilent 1200 HPLC was fitted with a 30 cm Aminex HPX-87H column equipped with a micro-guard cation H refill cartridge. The column was heated to 55° C. with the sample block being maintained at 25° C. The HPLC method comprised of 5 µl sample injection volume and an isocratic gradient comprised of 100% sulfuric acid (10 mM) was used as the mobile phase. The run time was a total of 25 minutes with acetyl phosphate eluting at 23.6 mins and pyruvate eluting at 16.0 minutes. A Refractive Index Detector (Agilent) was used after a 2 h equilibration period produced a stable baseline.

2.4 Optimization of Phosphate acetyltransferase (PTA): PTA was mixed with epoxy methacrylate resin and the immobilized enzyme was used to convert acetyl phosphate into acetyl-coenzyme A (acetyl-CoA). The reaction solution (10 mM Tris, 50 mM $KH_2PO_4$, 50 mM $K_2HPO_4$, pH 8.0, 5.0 mM $MgCl_2$, 100 mM NaCl, 3.2 mM acetyl phosphate, 3.2 mM CoA) was mixed with immobilized enzyme at 32° C. for 8 hours. Immobilized PTA (38.4 µM) was able to convert 60% of 3.2 mM acetyl phosphate for a yield of 1.92 mM (1.7 g/L) acetyl-CoA. For sampling, the reaction fluid was examined on an HPLC system to examine the amount of acetyl phosphate and acetyl-CoA. The HPLC method was as follows: An Agilent 1200 HPLC was fitted with a HYPERSIL ODS COLUMN 150 mm×3 mm equipped with a BetaSil C18 20 mm×2.1 mm guard column. The column was heated to 25° C. with the sample block being maintained at 4° C. HPLC method comprised of 5 µl sample injection volume and an isocratic mobile phase comprised of 75 mM $CH_3COONa$ (sodium acetate) and 100 mM $NaH_2PO_4$ (sodium dihydrogen phosphate) mixed with acetonitrile (ACN) in a ratio 94:6. The run time was a total of 12 minutes with acetyl-CoA eluting at 8.5 mins and coenzyme A (CoA) eluting at 3.9 minutes. A diode array detector (Agilent) was used for the detection of the molecule of interest at 259 nm.

2.5 Optimization of Acetyl-Coenzyme A C-acetyltransferase (PhaA): PhaA was mixed with epoxy methacrylate resin and the immobilized enzyme was used to convert acetyl-CoA into acetoacetyl-CoA. The reaction solution (50 mM Tris, 50 mM $KH_2PO_4$, 50 mM $K_2HPO_4$, pH 8.0, 5.0 mM $MgCl_2$, 100 mM NaCl, 2.5 mM acetyl CoA) was mixed with immobilized enzyme at 32° C. for 8 hours. Immobilized PhaA (20 µM) was able to convert 44% of 2.5 mM acetyl-CoA for a yield of 1.1 mM (1.1 g/L) acetoacetyl-CoA. The retention time of AcCoA and acetoacetyl CoA coincide; therefore, PhaA activity was measured based on the amount of CoA produced in the reaction, as CoA and acetoacetyl CoA are produced in equimolar amounts. For sampling, the reaction fluid was examined on an HPLC system to examine the amount of AcCoA and CoA. The HPLC method was as follows: An Agilent 1200 HPLC was fitted with a HYPERSIL ODS COLUMN 150 mm×3 mm equipped with a BetaSil C18 20 mm×2.1 mm guard column. The column was heated to 25° C. with the sample block being maintained at 4° C. HPLC method comprised of 5 µl sample injection volume and an isocratic mobile phase comprised of 75 mM $CH_3COONa$ and 100 mM $NaH_2PO_4$ mixed with ACN in a ratio 94:6. The run time was a total of 12 minutes with acetyl-coA eluting at 8.5 mins and coenzyme A eluting at 3.9 minutes. A diode array detector (Agilent) was used for the detection of the molecule of interest at 259 nm.

2.6 Optimization of Hydroxymethylglutaryl-CoA synthase (HMGS): HMGS was mixed with epoxy methacrylate resin and the immobilized enzyme was used to convert acetoacetyl CoA to HMG-CoA. The reaction solution (50 mM Tris 100 mM NaCl, 5 mM $MgCl_2$ pH 7.5, 5 mM acetoacetyl CoA) was mixed with 0.5 µM immobilized enzyme at 32° C. for 2 hours. After 2 hours, the reaction solution was incubated with 20.7 µM HMGR and 5 mM NADPH. HMGR is used to convert NADPH into NADP+ and thus reaction performance can be monitored at 340 nm. The coupled reaction was able to convert 54% of the starting material to mevalonic acid (2.7 mM or 416 mg/L). The activity of HMGR was measured by monitoring the loss of NADPH at 340 nm using a spectrophotometer.

2.7 Optimization of Hydroxymethylglutaryl-CoA reductase (HMGR): HMGR was mixed with epoxy methacrylate resin and the immobilized enzyme was used to convert NADPH into NADP+. The reaction solution (50 mM Tris, 100 mM NaCl, 5 mM $MgCl_2$ pH 7.0, 5 mM NADPH) was mixed with 0.4 µM immobilized enzyme at 32° C. for 2 hours. Immobilized HMGR was able to convert 98% of 5 mM (nicotinamide adenine dinucleotide phosphate (NADPH) for a yield of 4.9 mM NADP+ which is equimolar to mevalonic acid produced in the reaction (4.9 mM or 755 mg/L). The activity of HMGR was measured by monitoring the loss of NADPH at 340 nm using a spectrophotometer.

2.8 Optimization of Mevalonate Kinase (MVK): MVK was mixed with macroporous polymethacrylate resin and the immobilized enzyme was used to convert mevalonic acid into mevalonic acid-5-phosphate. Reaction solution (50 mM Tris, 5 mM $MgCl_2$, pH 8, 4 mM ATP, 4 mM mevalonic acid) was mixed with 133 µM immobilized enzyme at 37° C. for 8 hours. Immobilized MVK was able to convert 79% of 4 mM ATP for a yield of 3.16 mM (1.68 g/L) ADP. For sampling, the reaction mixture was examined on an HPLC system to examine the amount of adenosine triphosphate (ATP) and adenosine diphosphate (ADP). The HPLC method was as follows: An Agilent 1200 HPLC was fitted with a HYPERSIL ODS COLUMN 150 mm×3 mm equipped with a BetaSil C18 20 mm×2.1 mm guard column. The column was heated to 25° C. with the sample block being maintained at 4° C. HPLC method comprised of 5 µl sample injection volume and an isocratic mobile phase comprised of 100 mM $KH_2PO_4$ (potassium dihydrogen phosphate), 8 mM TBAHS (tetrabutylammonium hydrogen sulfate), pH 6.0, 20% methanol (v/v). The run time was a total of 10 minutes with ATP eluting at 5.7 mins and ADP eluting at 4.6 minutes. A diode array detector (Agilent) was used for the detection of the molecule of interest at 254 nm.

2.9 Optimization of Phosphomevalonate Kinase (PMVK): PMVK was mixed with amino $C_6$ methacrylate resin and the immobilized enzyme was used to convert mevalonic acid-5-phosphate into mevalonic acid-5-pyrophosphate. The reaction solution (50 mM Tris, 5 mM $MgCl_2$, pH 8, 4 mM ATP, 4 mM mevalonic acid-5-phosphate) was mixed with 160 µM immobilized enzyme at 37° C. for 32 hours. Immobilized MVK was able to convert 96% of 4 mM ATP for a yield of 3.84 mM (1.79 g/L) ADP. For sampling, the reaction fluid was examined on an HPLC system to examine the amount of ATP and ADP. The HPLC method was as follows: An Agilent 1200 HPLC was fitted with a HYPERSIL ODS COLUMN 150 mm×3 mm equipped with a BetaSil C18 20 mm×2.1 mm guard column. The column was heated to 25° C. with the sample block being maintained at 4° C. HPLC method comprised of 4 µl sample injection volume and an isocratic mobile phase comprised of 100 mM $KH_2PO_4$, 8 mM TBAHS, pH 6.0, 20% methanol (v/v). The run time was a total of 10 minutes with ATP eluting at 5.7 mins and ADP eluting at 4.6 minutes. A diode array detector (Agilent) was used for the detection of the molecule of interest at 254 nm.

2.10 Optimization of Diphosphomevalonate Kinase (MDC): MDC was mixed with epoxy methacrylate resin and the immobilized enzyme was used to convert mevalonic acid-5-pyrophosphate into isopentenyl pyrophosphate. Reaction solution (50 mM Tris, 5 mM $MgCl_2$, pH 8, 4 mM ATP, 4 mM mevalonic acid-5-pyrophosphate) was mixed with 160 µM immobilized enzyme at 37° C. for 32 hours. Immobilized MVK was able to convert 94% of 2 mM ATP for a yield of 1.8 mM (839 mg/L) ADP. For sampling, the reaction fluid was examined on an HPLC system to examine the amount of ATP and ADP. The HPLC method was as follows: An Agilent 1200 HPLC was fitted with a HYPERSIL ODS COLUMN 150 mm×3 mm equipped with a BetaSil C18 20 mm×2.1 mm guard column. The column was heated to 25° C. with the sample block being maintained at 4° C. HPLC method comprised of 5 µl sample injection volume and an isocratic mobile phase comprised of 100 mM $KH_2PO_4$, 8 mM TBAHS, pH 6.0, 20% methanol (v/v). The run time was a total of 10 minutes with ATP eluting at 5.7 mins and ADP eluting at 4.6 minutes. A diode array detector (DAD) was used for the detection of the molecule of interest at 254 nm.

2.11 Optimization of Isopentenyl-diphosphate Delta-isomerase (IDI): IDI was mixed with macroporous polymethacrylate resin and the immobilized enzyme was used to convert isopentenyl pyrophosphate (IPP) into dimethylallyl pyrophosphate (DMAPP). The reaction solution (50 mM Tris pH 8, 5 mM $MgCl_2$, 10 mM NaCl, 0.24 mM IPP) was mixed with 86 µM immobilized enzyme at 25° C. for 2 hours. Then, the reaction mixture was incubated with 0.24 mM olivetolic acid, 85 µM NphB, and 29.7 µM FPPS for 2 hours. Completed reactions were extracted 3× with ethyl acetate, evaporated, and then resuspended in methanol for analysis on an HPLC system to examine the amount of CBGA present in the reaction mixture. The coupled reaction was able to convert 28% of the starting material to 21.3 mg/L of the product. The HPLC method was as follows: An Agilent 1200 HPLC was fitted with a 250 mm×4.6 mm, 5 µm liChrospher RP8 column equipped with a guard column. The column was heated to 30° C. with the sample block being maintained at 25° C. HPLC method comprised of 5 µl sample injection volume and an isocratic mobile phase comprised of 25% buffer A (water, 0.1% formic acid, 5 mM ammonium formate) and 75% buffer B (acetonitrile, 0.1% formic acid, 5 mM ammonium formate). CBGA produced in the reaction was measured using DAD at 228 nm. The run time was a total of 10 minutes with CBGA eluting at 3.68 mins.

2.12 Optimization of Polyprenyl synthetase family protein (FPPS): FPPS was mixed with macroporous polymethacrylate resin and the immobilized enzyme was used to convert isopentenyl pyrophosphate (IPP) and dimethylallyl pyrophosphate (DMAPP) into geranyl pyrophosphate (GPP). The reaction solution (50 mM Tris pH 8, 5 mM $MgCl_2$, 10 mM NaCl, 0.24 mM IPP, 0.24 mM DMAPP, 0.24 mM olivetolic acid (OA)) and 120 µM NphB protein was mixed with 86 µM immobilized enzyme at 25° C. for 4 hours. Immobilized FPPS was able to convert 81% of 240 µM IPP and 240 µM DMAPP for a yield of 195 µM GPP. Analysis of GPP production is coupled to the activity of the prenyltransferase (NphB) that combines GPP and olivetolic acid to produce CBGA. Completed reactions were extracted 3× with ethyl acetate, evaporated, and resuspended in methanol for analysis on an HPLC system to examine the amount of CBGA present in the reaction mixture. The HPLC method was as follows: An Agilent 1200 HPLC was fitted with a 250 mm×4.6 mm, 5 µm LiChrospher RP8 column equipped with a guard column. The column was heated to 30° C. with the sample block being maintained at 25° C. HPLC method comprised of 5 µl sample injection volume and an isocratic mobile phase comprised of 25% buffer A (water, 0.1% formic acid, 5 mM ammonium formate) and 75% buffer B (acetonitrile, 0.1% formic acid, 5 mM ammonium formate). The coupled reaction yielded cannabigerolic acid (CBGA) at 129.6 µM or 41 mg/L. CBGA produced in the reaction was measured using DAD at 228 nm. The run time was a total of 10 minutes with CBGA eluting at 3.68 mins.

2.13 Optimization of Polyphosphate kinase 2 (PPK2): PPK2 was mixed with epoxy methacrylate resin and the immobilized enzyme was used to convert ADP into ATP to recycle this cofactor. Reaction solution (10 mM Tris pH 9, 10 mM $MgCl_2$, 10 mM NaCl, 5.0 mM poly-phosphate, 5.0 mM ADP) was mixed with 95 µM immobilized enzyme at 37° C. for 1 hour. Immobilized PPK2 was able to convert 5.0 mM ADP for a yield of 5.0 mM ATP (100%, 2.5 g/L). For sampling, the reaction fluid was examined on an HPLC system to examine the amount of ATP and ADP present in the reaction mixture. The HPLC method was as follows: An Agilent 1200 HPLC was fitted with a HYPERSIL ODS Column 150 mm×3 mm equipped with a BetaSil C18 20 mm×2.1 mm guard column. The column was heated to 25° C. with the sample block being maintained at 4° C. For each sample, 5 µL was injected and an isocratic mobile phase comprised of 100 mM $KH_2PO_4$, 8 mM TBAHS, pH 6.0, 20% methanol. The run time was a total of 10 minutes with ATP eluting at 5.7 mins and ADP eluting at 4.6 minutes. A diode array detector (DAD) was used for the detection of the molecule of interest at 254 nm.

2.14 Optimization of Glucose Dehydrogenase (GDH): GDH was mixed with epoxy methacrylate resin and the immobilized enzyme was used to convert NADP+ into NADPH to recycle this essential cofactor. The reaction solution (50 mM Tris pH 9, 20 mM glucose, 5.0 mM NADP+) was mixed with 200 µM immobilized enzyme at 22° C. for 15 minutes. Immobilized GDH was able to convert 5.0 mM NADP+ to yield 5.0 mM NADPH (100%, 3.7 g/L). The activity of GDH was detected by measuring the NADPH concentration of the reaction solution with a plate reader at 340 nm.

TABLE 2

Enzyme Sequences:

| Enzyme: | Sequence: | SEQ ID NO: |
|---|---|---|
| Maltose Binding Protein Alditol oxidase (MPB-ALDO) *Streptomyces coelicolor* A3 Accession: WP_011030685 | KIEEGKLVIWINGDKGYNGLAEVGKKFEKDTGIKVTVEHPD KLEEKFPQVAATGDGPDIIFWAHDRFGGYAQSGLLAEITPD KAFQDKLYPFTWDAVRYNGKLIAYPIAVEALSLIYNKDLLP NPPKTWEEIPALDKELKAKGKSALMFNLQEPYFTWPLIAAD GGYAFKYENGKYDIKDVGVDNAGAKAGLTFLVDLIKNKHMN ADTDYSIAEAAFNKGETAMTINGPWAWSNIDTSKVNYGVTV LPTFKGQPSKPFVGVLSAGINAASPNKELAKEFLENYLLTD EGLEAVNKDKPLGAVALKSYEEELAKDPRIAATMENAQKGE IMPNIPQMSAFWYAVRTAVINAASGRQTVDEALKDAQTRIT KGENLYFQGGMASMTGGQQMGRGSGMSDITVTNWAGNITYT AKELLRPHSLDALRALVADSARVRVLGSGHSFNEIAEPGDG GVLLSLAGLPSVVDVDTAARTVRVGGGVRYAELARVVHARG LALPNMASLPHISVAGSVATGTHGSGMGNGSLASMVREVEL VTADGSTVVIARGDERFGGAVTSLGALGVVTSLTLDLEPAY EMEQHVFTELPLAGLDPATFETVMAAAYSVSLFTDWRAPGF RQVWLKRRTDRPLDGFPYAAPATEKMHPVPGMPAVNCTEQF GVPGPWHERLPHFRAEFTPSSGAELQSEYLMPREHALAALH AMDAIRETLAPVLQTCEIRTVAADAQWLSPAYGRDTVAAHF TWVEDTAAVLPVVRRLEEALVPFAARPHWGKVFTVPAGELR ALYPRLADFGALARALDPAGKFTNAFVRGVLAG | 1 |
| Dihydroxy-acid dehydratase (DHAD) *Thermosynechococcus vulcanus* Accession: WP_126985616 | MAENWRSRIITEGVQRTPNRAMLRAVGFGDEDFNKPIVGVA SAHSTITPCNMGIAALASRAEAGIRAAGGMPQLFGTITVSD GISMGTEGMKYSLVSRDVIADSIETVCNAQSMDGVLAIGGC DKNMPGAMIAMARMNIPAIFVYGGTIKPGHWQGQDLTVVSA FEAVGQFSAGKMDEATLHAIEHHACPGAGSCGGMFTANTMS SAFEAMGMSLMYSSTMTAEDAEKADSTELAGKVLVEAIRKN IRPRDIITRKSIENAISVIMAVGGSTNAVLHFLAIAHSAEV PLTIDDFETIRQRVPVLCDLKPSGKYVTADLHRAGGIPQVM KMLLNAGLLHGDCLTITGETIAERLRHVPDTPDPNQDVIRP FDQPLYATGHLAILKGNLASEGAVAKISGVKNPQITGPARV FDSEEACLDAILAGKINPGDVIVIRYEGPVGGPGMREMLAP TSAIIGAGLGDSVGLITDGRFSGGTYGMVVGHVAPEAAVGG TIALVQEGDSITIDAHRRLLQLNVSEEELAARRAKWQPPAP RYTRGVLAKYAKLVSSSSLGAVTDRFV | 2 |
| Phosphate acetyltransferase (PTA) *Geobacillus stearothermophilus* Accession: WP_053532564 | MTTDLFTALKAKVTGTARKIVFPEGTDDRILTAASRLATEQ VLQPIVLGDEQAIRVKAAALGLPLEGVEIVNPRRYGGFDEL VSAFVERRKGKVTEETARELLFDENYFGTMLVYMGAADGLV SGAAHSTADTVRPALQIIKTKPGVDKTSGVFIMVRGDEKYV FADCAINIAPNSHDLAEIAVESARTAKMFGLKPRVVLLSFS TKGSASSPETEKVVEAVRLAKEMAPDLILDGEFQFDAAFVP EVAKKKAPDSVIQGDANVFIFPSLEAGNIGYKIAQRLGGFE AVGPILQGLNKPVNDLSRGCSAEDAYKLALITAAQSLGE | 3 |
| Acetyl-CoA C-acetyltransferase (PhaA) Multispecies *Cupriavidus* Accession: WP_010810132 | MTDVVIVSAARTAVGKFGGSLAKIPAPELGAVVIKAALERA GVKPEQVSEVIMGQVLTAGSGQNPARQAAIKAGLPAMVPAM TINKVCGSGLKAVMLAANAIMAGDAEIVVAGGQENMSAAPH VLPGSRDGFRMGDAKLVDTMIVDGLWDVYNQYHMGITAENV AKEYGITREAQDEFAVGSQNKAEAAQKAGKFDEEIVPVLIP QRKGDPVAFKTDEFVRQGATLDSMSGLKPAFDKAGTVTAAN ASGLNDGAAAVVVMSAAKAKELGLTPLATIKSYANAGVDPK VMGMGPVPASKRALSRAEWTPQDLDLMEINEAFAAQALAVH QQMGWDTSKVNVNGGAIAIGHPIGASGCRILVTLLHEMKRR DAKKGLASLCIGGGMGVALAVERK | 4 |
| Hydroxymethyl-glutaryl-CoA synthase (HMGS_A110G) *Enterococcus faecalis* Accession: WP_010785222 | MTIGIDKISFFVPPYYIDMTALAEARNVDPGKFHIGIGQDQ MAVNPISQDIVTFAANAAEAILTKEDKEAIDMVIVGTESSI DESKAAAVVLHRLMGIQPFARSFEIKEGCYGATAGLQLAKN HVALHPDKKVLVVAADIAKYGLNSGGEPTQGAGAVAMLVAS EPRILALKEDNVMLTQDIYDFWRPTGHPYPMVDGPLSNETY IQSFAQVWDEHKKRTGLDFADYDALAFHIPYTKMGKKALLA KISDQTEAEQERILARYEESIIYSRRVGNLYTSSLYLGLIS LLENATTLTAGNQIGLFSYGSGAVAEFFTGELVAGYQNHLQ KETHLALLDNRTELSIAEYEAMFAETLDTDIDQTLEDELKY SISAINNTVRSYRN | 5 |
| Hydroxymethyl-glutaryl-CoA reductase (HMGR) *Enterococcus faecalis* Accession: WP_002361742 | MKTVVIIDALRTPIGKYKGSLSQVSAVDLGTHVTTQLLKRH STISEEIDQVIFGNVLQAGNGQNPARQIAINSGLSHEIPAM TVNEVCGSGMKAVILAKQLIQLGEAEVLIAGGIENMSQAPK LQRFNYETESYDAPFSSMMYDGLTDAFSGQAMGLTAENVAE KYHVTREEQDQFSVHSQLKAAQAQAEGIFADEIAPLEVSGT LVEKDEGIRPNSSVEKGTLKTVFKEDGTVTAGNASTINDG ASALIIASQEYAEAHGLPYLAIIRDSVEVGIDPAYMGISPI KAIQKLLARNQLTTEEIDLYEINEAFAATSIVVQRELALPE EKVNIYGGGISLGHAIGATGARLLTSLSYQLNQKEKKYGVA | 6 |

TABLE 2-continued

Enzyme Sequences:

| Enzyme: | Sequence: | SEQ ID NO: |
|---|---|---|
| | SLCIGGGLGLAMLLERPQQKKNSRFYQMSPEERLASLLNEG QISADTKKEFENTALSSQIANHMIENQISETEVPMGVGLHL TVDETDYLVPMATEEPSVIAALSNGAKIAQGFKTVNQQRLM RGQIVFYDVADAESLIDELQVRETEIFQQAELSYPSIVKRG GGLRDLQYRAFDESFISVDFLVDVKDAMGANIVNAMLEGVA ELFREWFAEQKILFSILSNYATESVVTMKTAIPVSRLSKGS NGREIAEKIVLASRYASLDPYRAVTHNKGIMNGIEAVVLAT GNDTRAVSASCHAFAVKEGRYQGLTSWTLDGEQLIGEISVP LALATVGGATKVLPKSQAAADLLAVTDAKELSRVVAAVGLA QNLAALRALVSEGIQKGHMALQARSLAMTVGATGKEVEAVA QQLKRQKTMNQDRALAILNDLRKQ | |
| Mevalonate Kinase (MVK) *Methanosarcina mazei* Tuc01 Accession: AGF97182 | MLKFSKIEKLLRNNMVSCSAPGKIYLFGEHAVVYGETAIAC AVELRTRVRAELNDSITIQSQIGRTGLDFEKHPYVSAVIEK MRKSIPINGVFLTVDSDIPVGSGLGSSAAVTIASIGALNEL FGFGLSLQEIAKLGHEIE1KVQGAASPTDTYVSTFGGVVTI PERRKLKTPDCGIVIGDTGVFSSTKELVANVRQLRESYPDL IEPLMTSIGKISRIGEQLVLSGDYASIGRLMNVNQGLLDAL GVNILELSQLIYSARAAGAFGAKITGAGGGGCMVALTAPEK CNQVAEAIAGAGGKVTITKPTEQGLKVD | 7 |
| Phosphomevalonate Kinase (PMVK) *Streptococcus pneumoniae* Accession: WP_000562411 | MIAVKTCGKLYWAGEYAILEPGQLALIKDIPIYMRAEIAFS DSYRIYSDMFDFAVDLRPNPDYSLIQETIALMGDFLAVRGQ NLRPFSLAIYGKMEREGKKFGLGSSGSVVVLVVKALLALYN LSVDQNLLFKLTSAVLLKRGDNGSMGDLACIAAEDLVLYQS FDRQKVAAWLEEENLATVLERDWGFSISQVKPTLECDFLVG WTKEVAVSSHMVQQIKQNINQNFLTSSKETVVSLVEALEQG KSEKIIEQVEVASKLLEGLSTDIYTPLLRQLKEASQDLQAV AKSSGAGGGDCGIALSFDAQSTKTLKNRWADLGIELLYQER IGHDDKS | 8 |
| Diphosphomevalonate Kinase (MDC) *Streptococcus pneumoniae* R6 Accession: AAK99143 | MYHSLGNQFDTRTRTSRKIRRERSCSDMDREPVTVRSYANI AIIKYWGKKKEKEMVPATSSISLTLENMYTETTLSPLPANV TADEFYINGQLQNEVEHAKMSKIIDRYRPAGEGFVRIDTQN NMPTAAGLSSSSSGLSALVKACNAYFKLGLDRSQLAQEAKF ASGSSSRSFYGPLGAWDKDSGEIYPVETDLKLAMIMLVLED KKKPISSRDGMKLCVETSTTFDDVVVRQSEKDYQDMLIYLK ENDFAKIGELTEKNALAMHATTKTASPAFSYLTDASYEAMD FVRQLREKGEACYFTMDAGPNVKVFCQEKDLEHLSEIFGQR YRLIVSKTKDLSQDDCC | 9 |
| Isopentenyl-diphosphate Delta-isomerase (IDI) Multispecies Bacteria Accession: WP_001192820 | MQTEHVILLNAQGVPTGTLEKYAAHTADTRLHLAFSSWLFN AKGQLLVTRRALSKKAWPGVWTNSVCGHPQLGESNEDAVIR RCRYELGVEITPPESIYPDFRYRATDPSGIVENEVCPVFAA RTTSALQINDDEVMDYQWCDLADVLHGIDATPWAFSPWMVM QATNREARKRLSAFTQLK | 10 |
| Polyprenyl synthetase family protein (FPPS S82F) *Geobacillus stearothermophilus* Accession: WP_033016440 | MAQLSVEQFLNEQKQAVETALSRYIERLEGPAKLKKAMAYS LEAGGKRIRPLLLLSTVRALGKDPAVGLPVACAIEMIHTYF LIHDDLPSMDNDDLRRGKPTNHKVFGEAMAILAGDGLLTYA FQLITEIDDERIPPSVRLRLIERLAKAAGPEGMVAGQAADM EGEGKTLTLSELEYIHRHKTGKMLQYSVHAGALIGGADARQ TRELDEFAAHLGLAFQIRDDILDIEGAEEKIGKPVGSDQSN NKATYPALLSLAGAKEKLAFHIEAAQRHLRNADVDGAALAY ICELVAARDH | 11 |
| Polyphosphate kinse 2 (PPK2) *Rhizobacteria* Accession: WP_010968631 | MALDEAPAEARPGSRAVELEIDGRSRIFDIDDPDLPKWIDE EAFRSDDYPYKKKLDREEYEETLTKLQIELVKVQFWMQATG KRVMAVFEGRDAAGKGGAIHATTANMNPRSARVVALTKPTE TERGQWYFQRYVATFPTAGEFVLFDRSWYNRAGVEPVMGFC TPDQYEQFLKEAPRFEEMIANEGIHLFKFWINIGREMQLKR FHDRRHDPLKIWKLSPMDIAALSKWDDYTGKRDRMLKETHT EHGPWAVIRGNDKRRSINVIRHMLTKLDYDGKDEAAIGEV DEKILGSGPGFLR | 12 |

TABLE 2-continued

Enzyme Sequences:

| Enzyme: | Sequence: | SEQ ID NO: |
|---|---|---|
| Glucose Dehydrogenase (GDH) Bacillus sp. G3 Accession: GQ402830.1 | MYSDLEGKWVITGSASGLGRAMGVRFAREKAKWINYRSRES EANDVLEEIKKVGGEAIAVKGDVTVESDVVNLIQSAVKEFG TLDVMINNAGIENAVPSHEMPLEDWNRVINTNLTGAFLGSR EAIKYFVEHDIKGSVINMSSVHEKIPWPLFVHYAASKGGMK LMTETLAMEYAPKGIRVNNIGPGAINTPINAEKFADPKKRA DVESMIPMGYIGKPEEIAAVATWLASSEASYVTGITLFADG GMTLYPSFQAGRG | 13 |

*Note:
Pyruvate Oxidase (PyOx, Aerococcus viridans) was purchased from AG Scientific, product P-1600.

3.0 Use of all immobilized Enzymes to create GPP from glycerol: After demonstrating generation of GPP from glycerol with free enzymes, and also demonstrating that all of the required individual enzymes are active when immobilized, the next aim was to generate GPP from glycerol using immobilized enzymes. Each enzyme was immobilized onto 10 mg of resin as listed in Table 3. Purified enzymes were mixed with resin for 18 hours at 21° C. and immobilized enzymes were pooled into a single tube.

TABLE 3

Specifics for immobilized enzyme batch reactions.

| Enzyme Name | Amount (mg) | Resin |
|---|---|---|
| MBP-Aldo (Aldo) | 0.5 | Amino $C_6$ methacrylate |
| Dihydroxy Acid Dehydratase (DHAD) | 0.5 | Amino $C_6$ methacrylate |
| Pyruvate Oxidase (PyOx) | 0.25 | Amino $C_6$ methacrylate |
| Acetyl-phosphate transferase (PTA) | 0.15 | Epoxy methacrylate |
| Acetyl-CoA acetyltransferase (PhaA) | 0.1 | Epoxy methacrylate |
| HMG-CoA Synthase A110G (HMGS) | 0.15 | Epoxy methacrylate |
| HMG-CoA Reductase (HMGR) | 0.4 | Epoxy methacrylate |
| Mevalonate Kinase (MVK) | 0.2 | Macroporous polymethacrylate |
| Phosphomevalonate Kinase (PMVK) | 0.2 | Amino $C_6$ methacrylate |
| Diphosphomevalonate Kinase (MDC) | 0.4 | Epoxy methacrylate |
| Isopentyl-PP Isomerase (IDI) | 0.35 | Macroporous polymethacrylate |
| Farnesyl-PP synthase S82F (FPPS) | 0.2 | Macroporous polymethacrylate |
| Prenyl Transferase (NphB) | 0.2 | Macroporous polymethacrylate |

Figure 2A:
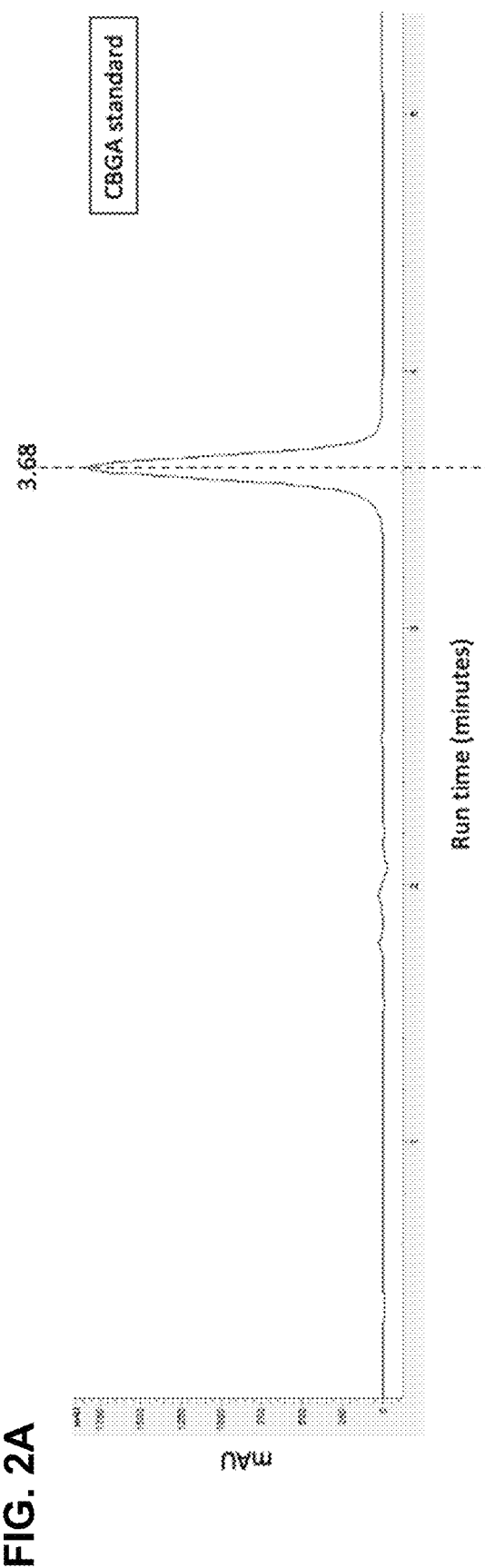
FIGS. 2A and 2B show HPLC traces for cannabigerolic acid (CBGA) for both CBGA standards (top, FIG. 2A) and immobilized enzyme batch reactions (bottom, FIG. 2B). The retention time of 3.68 minutes at 228 nm is noted for both reactions.
Figure 2B:
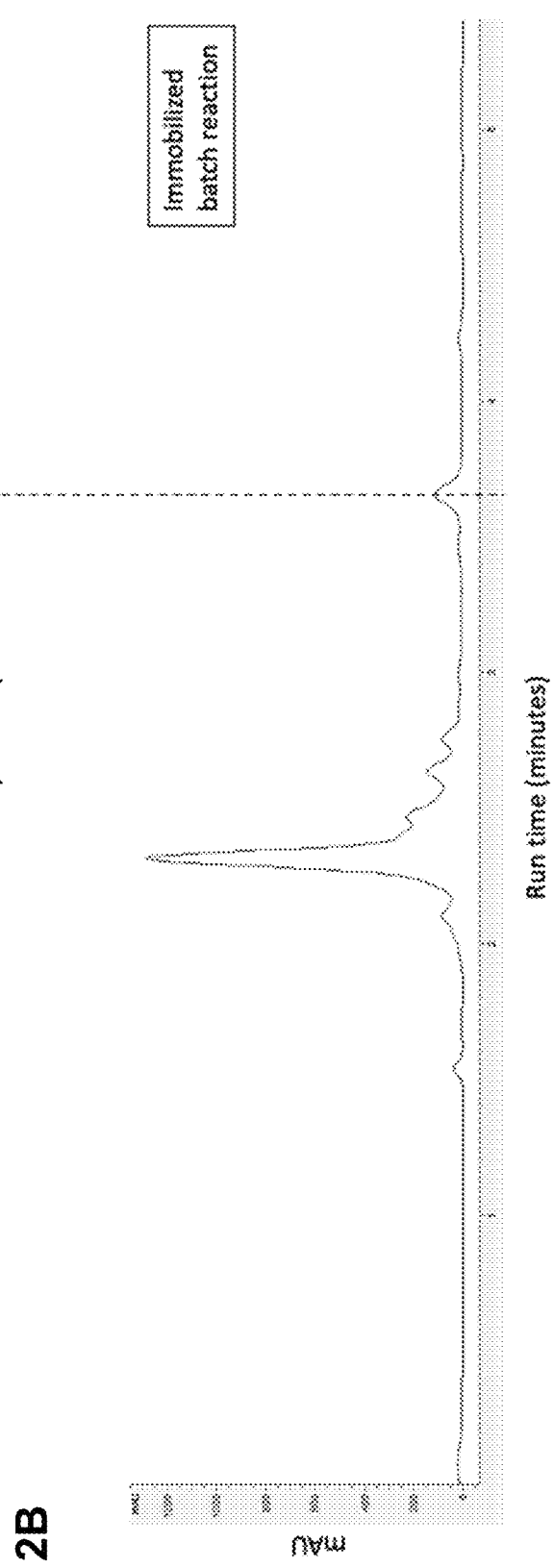

For this multi-step reaction, the first three enzymes (Aldo, DHAD, and PyOX) were first added sequentially into the batch reactor. First, immobilized MBP-Aldo was added to reaction solution (50 mM Tris pH 9, 2.5 mM $MgCl_2$, 10 mM glycerol) for 18 h at 37° C. Next, immobilized DHAD was added to the reaction solution and incubated for 18 h at 45° C. The supernatant was removed from the immobilized enzymes, and the reaction solution was adjusted to contain 50 mM NaCl, 20 mM potassium phosphate (pH 6.5), 10 mM thiamine pyrophosphate, and finally, the pH of the reaction solution was adjusted to pH 6.0. Immobilized PyOx was then added to the reaction solution for 16 h at 37° C. The supernatant was then removed from immobilized enzyme and the reaction solution was adjusted to contain 50 mM Tris, 20 mM potassium phosphate, 2.5 mM $MgCl_2$, 50 mM NaCl, 10 mM NADPH, 10 mM ATP, 10 mM CoA, 4 mM olivetolic acid, and pH 8.0 for a final volume of 1.0 mL. The remaining ten immobilized enzymes in this pathway were added to the reaction mixture. The reactions were carried out for five days at 37° C. and were then extracted ethyl acetate (2×200 µL), evaporated under reduced pressure, and resuspended in methanol (1 mL) for analysis on a HPLC system to examine the amount of CBGA present in the reaction mixture. The HPLC method was as follows: An Agilent 1200 HPLC was fitted with a 250 mm×4.6 mm, 5 µm liChrospher RP8 column equipped with a guard column. The column was heated to 30° C. with the sample block being maintained at 25° C. HPLC method comprised of 5 µl sample injection volume and an isocratic gradient comprised of 25% buffer A (water, 0.1% formic acid, 5 mM ammonium formate) and 75% buffer B (acetonitrile, 0.1% formic acid, 5 mM ammonium formate) was used as the mobile phase. The reaction yielded cannabigerolic acid (CBGA) at 155 µM or 49 mg/L (FIGS. 2A and 2B). CBGA produced in the reaction was measured using DAD at 228 nm. The run time was a total of 10 minutes with CBGA eluting at 3.68 minutes.

4.0 Use of Immobilized Enzymes to create GPP from Glycerol with Cofactors (ATP and NADPH recycling): In addition to demonstrating the immobilized glycerol to GPP pathway success, the recycling of two common cofactors (ATP and NADPH) in the reaction was achieved. The immobilized enzyme composition shown in Table 4 was used in the reaction.

TABLE 4

Specifics for immobilized cofactor recycling enzymes for batch reactions.

| Enzyme Name | Amount (mg) | Resin |
|---|---|---|
| Polyphosphate kinase 2 (PPK2) | 0.1 | Epoxy methacrylate |
| Glucose dehydrogenase (GDH) | 0.1 | Epoxy methacrylate |
| MBP-Aldo (Aldo) | 0.5 | Amino $C_6$ methacrylate |
| Dihydroxy Acid Dehydratase (DHAD) | 0.5 | Amino $C_6$ methacrylate |
| Pyruvate Oxidase (PyOx) | 0.25 | Amino $C_6$ methacrylate |
| Acetyl-phosphate transferase (PTA) | 0.15 | Epoxy methacrylate |
| Acetyl-CoA acetyltransferase (PhaA) | 0.1 | Epoxy methacrylate |
| HMG-CoA Synthase A110G (HMGS) | 0.15 | Epoxy methacrylate |
| HMG-CoA Reductase (HMGR) | 0.4 | Epoxy methacrylate |
| Mevalonate Kinase (MVK) | 0.2 | Macroporous polymethacrylate |
| Phosphomevalonate Kinase (PMVK) | 0.2 | Amino $C_6$ methacrylate |
| Diphosphomevalonate Kinase (MDC) | 0.4 | Epoxy methacrylate |
| Isopentyl-PP Isomerase (IDI) | 0.35 | Macroporous polymethacrylate |
| Farnesyl-PP synthase S82F (FPPS) | 0.2 | Macroporous polymethacrylate |
| Prenyl Transferase (NphB) | 0.2 | Macroporous polymethacrylate |

For this multi-step reaction, the first three enzymes (Aldo, DHAD, and PyOX) were first added sequentially into the batch reactor. First, immobilized MBP-Aldo was added to reaction solution (50 mM Tris pH 9, 2.5 mM $MgCl_2$, 10 mM glycerol) for 18 h at 37° C. Next, immobilized DHAD was added to the reaction solution and incubated for 18 h at 45° C. The supernatant was removed from the immobilized enzymes, and the reaction solution was adjusted to contain 50 mM NaCl, 20 mM potassium phosphate (pH 6.5), 10 mM thiamine pyrophosphate, and finally, the pH of the reaction solution was adjusted to pH 6.0. Immobilized PyOx was then added to the reaction solution for 16 h at 37° C. The supernatant was then removed from immobilized enzyme and the reaction solution was adjusted to contain 50 mM Tris, 20 mM potassium phosphate, 2.5 mM $MgCl_2$, 50 mM NaCl, 10 mM NADPH, 10 mM ATP, 10 mM CoA, 4 mM olivetolic acid, and pH 8.0 for a final volume of 1.0 mL. The remaining 12 enzymes (as shown in Table 4) were added to a reaction solution of 50 mM Tris, 20 mM potassium phosphate, 2.5 mM $MgCl_2$, 50 mM NaCl, 3.3 mM NADPH, 3.3 mM ATP, 5.0 mM poly-phosphate, 5.0 mM glucose 10 mM CoA, 4 mM olivetolic acid and pH 8.0 in a final volume of 1.0 mL. Batch reactions continued for 5 days at 37° C. and were then extracted with ethyl acetate (3×200 µL), evaporated under reduced pressure, and resuspended in methanol (1 mL) for analysis on a HPLC system to examine the amount of CBGA present in the reaction mixture. The HPLC method was as follows: An Agilent 1200 HPLC was fitted with a 250 mm×4.6 mm, 5 µm liChrospher RP8 column equipped with a guard column. The column was heated to 30° C. with the sample block being maintained at 25° C. The HPLC method comprised of a 5 µl sample injection volume and a mobile phase comprised of 25% buffer A (water, 0.1% formic acid, 5 mM ammonium formate) and 75% buffer B (acetonitrile, 0.1% formic acid, 5 mM ammonium formate). The reaction yielded cannabigerolic acid (CBGA) at 114 µM or 36 mg/L. CBGA produced in the reaction was measured using DAD at 228 nm. The run time was a total of 10 minutes with CBGA eluting at 3.68 mins.

EMBODIMENTS

The following embodiments are intended to be illustrative only and not to be limiting in any way.

Embodiment 1: A method of converting glycerol to geranyl pyrophosphate (GPP) and additional secondary metabolites, the method comprising (a) adding glycerol to a reaction mixture; (b) adding a plurality of enzymes to the reaction mixture from (a), wherein the enzymes are selected from a group consisting of alditol oxidase (Aldo), dihydroxy-acid dehydratase (DHAD), pyruvate oxidase (PyOx), acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), and farnesyl-PP synthase S82F (FPPS); (c) removing a supernatant from the reaction mixture from (b); and isolating or producing GPP.

Embodiment 2: The method of embodiment 1, wherein at least two enzymes are added to the reaction mixture.

Embodiment 3: The method of embodiment 1 or embodiment 2, wherein at least five enzymes are added to the reaction mixture.

Embodiment 4: The method of any one of embodiments 1-3, wherein at least ten enzymes are added to the reaction mixture.

Embodiment 5: The method of any one of embodiments 1-4, further comprising adding a NphB enzyme to step (b) to convert GPP to (cannabigerolic acid) CBGA Embodiment 6: The method of embodiment 5, wherein the conversion of GPP to CBGA is used to determine the amount of GPP produced from the method.

Embodiment 7: The method of any one of embodiments 1-6, wherein the reaction mixture comprises co-factors.

Embodiment 8: The method of embodiment 7, wherein the cofactors are adenosine triphosphate (ATP), nicotinamide adenine dinucleotide ($NAD^+$), nicotinamide adenine dinucleotide phosphate ($NADP^+$), or a combination thereof.

Embodiment 9: The method of embodiment 7 or embodiment 8, wherein the cofactor are recycled.

Embodiment 10: The method of embodiment 9, wherein glucose dehydrogenase (GDH), and polyphosphate kinase 2 (PPK2) are added to the reaction mixture to recycle the co-factors.

Embodiment 11: The method of claim any one of embodiments 1-10, wherein one or more of the enzymes are immobilized.

Embodiment 12: The method of claim any one of embodiments 1-10, wherein the plurality of enzymes are immobilized Embodiment 13: The method of claim any one of embodiments 1-10, wherein one or more of the enzymes are non-immobilized.

Embodiment 14: The method of claim any one of embodiments 1-10, wherein the plurality of enzymes are non-immobilized.

Embodiment 15: A method of converting glycerol to geranyl pyrophosphate (GPP) and additional secondary metabolites, the method comprising (a) adding glycerol and alditol oxidase (Aldo) to a reaction mixture; (b) adding dihydroxy-acid dehydratase (DHAD) to the reaction mixture from (a); (c) removing a supernatant of the reaction mixture from (b); (d) adding pyruvate oxidase (PyOx) to the supernatant of the reaction mixture from (c); (e) removing a supernatant of the reaction mixture from (d); (f) adding at least two enzymes selected from a group consisting of acetyl-phosphate transferase (PTA), acetyl-CoA acetyltransferase (PhaA), HMG-CoA Synthase A110G (HMGS), HMG-CoA Reductase (HMGR), mevalonate kinase (MVK), phosphomevalonate kinase (PMVK), diphosphomevalonate kinase (MDC), isopentyl-PP Isomerase (IDI), farnesyl-PP synthase S82F (FPPS), and prenyl transferase (NphB) to the supernatant of the reaction mixture from (e); (g) removing a supernatant from the reaction mixture from (f); and (h) isolating GPP.

Embodiment 16: The method of embodiment 15 further comprising adding a NphB enzyme to step (f) to convert GPP to (cannabigerolic acid) CBGA.

Embodiment 17: The method of embodiment 16, wherein the conversion of GPP to CBGA is used to determine the amount of GPP produced from the method.

Embodiment 18: The method of any one of embodiments 15-17, wherein the reaction mixture comprises co-factors.

Embodiment 19: The method of embodiment 18, wherein the cofactors are adenosine triphosphate (ATP), nicotinamide adenine dinucleotide ($NAD^+$), nicotinamide adenine dinucleotide phosphate ($NADP^+$), or a combination thereof.

Embodiment 20: The method of embodiment 17 or embodiment 18, wherein the cofactor are recycled.

Embodiment 21: The method of embodiment 20, wherein glucose dehydrogenase (GDH), and polyphosphate kinase 2 (PPK2) are added to the reaction mixture to recycle the co-factors.

Embodiment 22: The method of claim any one of embodiments 15-21, wherein one or more of the enzymes are immobilized.

Embodiment 23: The method of claim any one of embodiments 15-21, wherein the plurality of enzymes are immobilized Embodiment 24: The method of claim any one of embodiments 15-21, wherein one or more of the enzymes are non-immobilized.

Embodiment 25: The method of claim any one of embodiments 15-21, wherein the plurality of enzymes are non-immobilized.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of converting glycerol to geranyl pyrophosphate (GPP) and additional secondary metabolites in a cell-free medium, the method comprising:
   a) adding glycerol to a reaction mixture;
   b) adding a plurality of enzymes to the reaction mixture from (a); wherein the plurality of enzymes comprises an enzyme that comprises SEQ ID NO: 1 (maltose binding protein alditol oxidase (MPD-ALDO) or an optimized form thereof, and one or more enzymes selected from the group consisting of: an enzyme that comprises SEQ ID NO: 2 (dihydroxy-acid dehydratase (DHAD)) or an optimized form thereof, an enzyme that comprises SEQ ID NO: 3 (acetyl-phosphate transferase (PTA)) or an optimized form thereof, an enzyme that comprises SEQ ID NO: 4 (acetyl-CoA acetyltransferase (PhaA)) or an optimized form thereof, an enzyme that comprises SEQ ID NO: 5 (HMG-CoA Synthase A110G (HMGS)) or an optimized form thereof, an enzyme that comprises SEQ ID NO: 6 (HMG-CoA Reductase (HMGR)) or an optimized form thereof, an enzyme that comprises SEQ ID NO: 7 (mevalonate kinase (MVK)) or an optimized form thereof, an enzyme that comprises SEQ ID NO: 8 (phosphomevalonate kinase (PMVK)) or an optimized form thereof, an enzyme that comprises SEQ ID NO: 9 (diphosphomevalonate kinase (MDC)) or an optimized form thereof, and an enzyme that comprises SEQ ID NO: 10 (isopentyl-PP Isomerase (IDI)) or an optimized form thereof;
   c) removing a supernatant from the reaction mixture from (b); and
   d) isolating GPP.

2. The method of claim 1, wherein at least five enzymes are added to the reaction mixture.

3. The method of claim 1, wherein at least ten enzymes are added to the reaction mixture.

4. The method of claim 1, further comprising adding a phenyl transferase enzyme to step (b) to convert GPP to cannabigerolic acid (CBGA).

5. The method of claim 4, wherein the conversion of GPP to CBGA is used to determine the amount of GPP produced from the method.

6. The method of claim 1, wherein the reaction mixture comprises co-factors.

7. The method of claim 6, wherein the cofactors are adenosine triphosphate (ATP), nicotinamide adenine dinucleotide ($NAD^+$), nicotinamide adenine dinucleotide phosphate ($NADP^+$), or a combination thereof.

8. The method of claim 6, wherein the cofactors are recycled.

9. The method of claim 8, wherein glucose dehydrogenase (GDH), and polyphosphate kinase 2 (PPK2) are added to the reaction mixture to recycle the co-factors.

10. The method of claim 1, wherein one or more of the enzymes are immobilized.

11. The method of claim 1, wherein one or more of the enzymes are non-immobilized.

12. The method of claim 1, wherein the plurality of enzymes in the reaction mixture comprises all of the plurality of enzymes from step (b).

13. The method of claim 12, wherein the enzymes in the reaction mixture are immobilized.

14. The method of claim 9, wherein the PPK2 enzyme comprises SEQ ID NO: 12 or an optimized form thereof.

15. The method of claim 9, wherein the GDH enzyme has comprises SEQ ID NO: 13 or an optimized form thereof.

\* \* \* \* \*

SEQUENCE LISTING

```
<160> NUMBER OF SEQ ID NOS: 13

<210> SEQ ID NO 1
<211> LENGTH: 812
<212> TYPE: PRT
<213> ORGANISM: Unknown
<220> FEATURE:
<223> OTHER INFORMATION: Streptomyces coelicolor

<400> SEQUENCE: 1

Lys Ile Glu Glu Gly Lys Leu Val Ile Trp Ile Asn Gly Asp Lys Gly
1               5                   10                  15

Tyr Asn Gly Leu Ala Glu Val Gly Lys Lys Phe Glu Lys Asp Thr Gly
                20                  25                  30

Ile Lys Val Thr Val Glu His Pro Asp Lys Leu Glu Glu Lys Phe Pro
            35                  40                  45

Gln Val Ala Ala Thr Gly Asp Gly Pro Asp Ile Ile Phe Trp Ala His
        50                  55                  60

Asp Arg Phe Gly Gly Tyr Ala Gln Ser Gly Leu Leu Ala Glu Ile Thr
65                  70                  75                  80

Pro Asp Lys Ala Phe Gln Asp Lys Leu Tyr Pro Phe Thr Trp Asp Ala
                85                  90                  95

Val Arg Tyr Asn Gly Lys Leu Ile Ala Tyr Pro Ile Ala Val Glu Ala
                100                 105                 110

Leu Ser Leu Ile Tyr Asn Lys Asp Leu Leu Pro Asn Pro Pro Lys Thr
            115                 120                 125

Trp Glu Glu Ile Pro Ala Leu Asp Lys Glu Leu Lys Ala Lys Gly Lys
130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Glu Asn Gly Lys Tyr
                165                 170                 175

Asp Ile Lys Asp Val Gly Val Asp Asn Ala Gly Ala Lys Ala Gly Leu
            180                 185                 190

Thr Phe Leu Val Asp Leu Ile Lys Asn Lys His Met Asn Ala Asp Thr
        195                 200                 205

Asp Tyr Ser Ile Ala Glu Ala Ala Phe Asn Lys Gly Glu Thr Ala Met
    210                 215                 220

Thr Ile Asn Gly Pro Trp Ala Trp Ser Asn Ile Asp Thr Ser Lys Val
225                 230                 235                 240

Asn Tyr Gly Val Thr Val Leu Pro Thr Phe Lys Gly Gln Pro Ser Lys
                245                 250                 255

Pro Phe Val Gly Val Leu Ser Ala Gly Ile Asn Ala Ala Ser Pro Asn
```

```
            260                 265                 270
Lys Glu Leu Ala Lys Glu Phe Leu Glu Asn Tyr Leu Thr Asp Glu
        275                 280                 285

Gly Leu Glu Ala Val Asn Lys Asp Lys Pro Leu Gly Ala Val Ala Leu
        290                 295                 300

Lys Ser Tyr Glu Glu Glu Leu Ala Lys Asp Pro Arg Ile Ala Ala Thr
305                 310                 315                 320

Met Glu Asn Ala Gln Lys Gly Glu Ile Met Pro Asn Ile Pro Gln Met
                325                 330                 335

Ser Ala Phe Trp Tyr Ala Val Arg Thr Ala Val Ile Asn Ala Ala Ser
            340                 345                 350

Gly Arg Gln Thr Val Asp Glu Ala Leu Lys Asp Ala Gln Thr Arg Ile
        355                 360                 365

Thr Lys Gly Glu Asn Leu Tyr Phe Gln Gly Gly Met Ala Ser Met Thr
        370                 375                 380

Gly Gly Gln Gln Met Gly Arg Gly Ser Gly Met Ser Asp Ile Thr Val
385                 390                 395                 400

Thr Asn Trp Ala Gly Asn Ile Thr Tyr Thr Ala Lys Glu Leu Leu Arg
                405                 410                 415

Pro His Ser Leu Asp Ala Leu Arg Ala Leu Val Ala Asp Ser Ala Arg
            420                 425                 430

Val Arg Val Leu Gly Ser Gly His Ser Phe Asn Glu Ile Ala Glu Pro
        435                 440                 445

Gly Asp Gly Gly Val Leu Leu Ser Leu Ala Gly Leu Pro Ser Val Val
        450                 455                 460

Asp Val Asp Thr Ala Ala Arg Thr Val Arg Val Gly Gly Gly Val Arg
465                 470                 475                 480

Tyr Ala Glu Leu Ala Arg Val Val His Ala Arg Gly Leu Ala Leu Pro
                485                 490                 495

Asn Met Ala Ser Leu Pro His Ile Ser Val Ala Gly Ser Val Ala Thr
            500                 505                 510

Gly Thr His Gly Ser Gly Met Gly Asn Gly Ser Leu Ala Ser Met Val
        515                 520                 525

Arg Glu Val Glu Leu Val Thr Ala Asp Gly Ser Thr Val Val Ile Ala
        530                 535                 540

Arg Gly Asp Glu Arg Phe Gly Gly Ala Val Thr Ser Leu Gly Ala Leu
545                 550                 555                 560

Gly Val Val Thr Ser Leu Thr Leu Asp Leu Glu Pro Ala Tyr Glu Met
                565                 570                 575

Glu Gln His Val Phe Thr Glu Leu Pro Leu Ala Gly Leu Asp Pro Ala
            580                 585                 590

Thr Phe Glu Thr Val Met Ala Ala Tyr Ser Val Ser Leu Phe Thr
        595                 600                 605

Asp Trp Arg Ala Pro Gly Phe Arg Gln Val Trp Leu Lys Arg Arg Thr
        610                 615                 620

Asp Arg Pro Leu Asp Gly Phe Pro Tyr Ala Ala Pro Ala Thr Glu Lys
625                 630                 635                 640

Met His Pro Val Pro Gly Met Pro Ala Val Asn Cys Thr Glu Gln Phe
                645                 650                 655

Gly Val Pro Gly Pro Trp His Glu Arg Leu Pro His Phe Arg Ala Glu
            660                 665                 670

Phe Thr Pro Ser Ser Gly Ala Glu Leu Gln Ser Glu Tyr Leu Met Pro
        675                 680                 685
```

-continued

```
Arg Glu His Ala Leu Ala Ala Leu His Ala Met Asp Ala Ile Arg Glu
    690                 695                 700

Thr Leu Ala Pro Val Leu Gln Thr Cys Glu Ile Arg Thr Val Ala Ala
705                 710                 715                 720

Asp Ala Gln Trp Leu Ser Pro Ala Tyr Gly Arg Asp Thr Val Ala Ala
                725                 730                 735

His Phe Thr Trp Val Glu Asp Thr Ala Ala Val Leu Pro Val Val Arg
            740                 745                 750

Arg Leu Glu Glu Ala Leu Val Pro Phe Ala Ala Arg Pro His Trp Gly
        755                 760                 765

Lys Val Phe Thr Val Pro Ala Gly Glu Leu Arg Ala Leu Tyr Pro Arg
    770                 775                 780

Leu Ala Asp Phe Gly Ala Leu Ala Arg Ala Leu Asp Pro Ala Gly Lys
785                 790                 795                 800

Phe Thr Asn Ala Phe Val Arg Gly Val Leu Ala Gly
                805                 810

<210> SEQ ID NO 2
<211> LENGTH: 560
<212> TYPE: PRT
<213> ORGANISM: Unknown
<220> FEATURE:
<223> OTHER INFORMATION: Thermosynechococcus vulcanus

<400> SEQUENCE: 2

Met Ala Glu Asn Trp Arg Ser Arg Ile Ile Thr Glu Gly Val Gln Arg
1               5                   10                  15

Thr Pro Asn Arg Ala Met Leu Arg Ala Val Gly Phe Gly Asp Glu Asp
            20                  25                  30

Phe Asn Lys Pro Ile Val Gly Val Ala Ser Ala His Ser Thr Ile Thr
        35                  40                  45

Pro Cys Asn Met Gly Ile Ala Ala Leu Ala Ser Arg Ala Glu Ala Gly
    50                  55                  60

Ile Arg Ala Ala Gly Gly Met Pro Gln Leu Phe Gly Thr Ile Thr Val
65                  70                  75                  80

Ser Asp Gly Ile Ser Met Gly Thr Glu Gly Met Lys Tyr Ser Leu Val
                85                  90                  95

Ser Arg Asp Val Ile Ala Asp Ser Ile Glu Thr Val Cys Asn Ala Gln
            100                 105                 110

Ser Met Asp Gly Val Leu Ala Ile Gly Gly Cys Asp Lys Asn Met Pro
        115                 120                 125

Gly Ala Met Ile Ala Met Ala Arg Met Asn Ile Pro Ala Ile Phe Val
    130                 135                 140

Tyr Gly Gly Thr Ile Lys Pro Gly His Trp Gln Gly Gln Asp Leu Thr
145                 150                 155                 160

Val Val Ser Ala Phe Glu Ala Val Gly Gln Phe Ser Ala Gly Lys Met
                165                 170                 175

Asp Glu Ala Thr Leu His Ala Ile Glu His His Ala Cys Pro Gly Ala
            180                 185                 190

Gly Ser Cys Gly Gly Met Phe Thr Ala Asn Thr Met Ser Ser Ala Phe
        195                 200                 205

Glu Ala Met Gly Met Ser Leu Met Tyr Ser Ser Thr Met Thr Ala Glu
    210                 215                 220

Asp Ala Glu Lys Ala Asp Ser Thr Glu Leu Ala Gly Lys Val Leu Val
225                 230                 235                 240
```

-continued

```
Glu Ala Ile Arg Lys Asn Ile Arg Pro Arg Asp Ile Ile Thr Arg Lys
                245                 250                 255

Ser Ile Glu Asn Ala Ile Ser Val Ile Met Ala Val Gly Gly Ser Thr
            260                 265                 270

Asn Ala Val Leu His Phe Leu Ala Ile Ala His Ser Ala Glu Val Pro
        275                 280                 285

Leu Thr Ile Asp Asp Phe Glu Thr Ile Arg Gln Arg Val Pro Val Leu
    290                 295                 300

Cys Asp Leu Lys Pro Ser Gly Lys Tyr Val Thr Ala Asp Leu His Arg
305                 310                 315                 320

Ala Gly Gly Ile Pro Gln Val Met Lys Met Leu Leu Asn Ala Gly Leu
                325                 330                 335

Leu His Gly Asp Cys Leu Thr Ile Thr Gly Glu Thr Ile Ala Glu Arg
            340                 345                 350

Leu Arg His Val Pro Asp Thr Pro Asp Pro Asn Gln Asp Val Ile Arg
        355                 360                 365

Pro Phe Asp Gln Pro Leu Tyr Ala Thr Gly His Leu Ala Ile Leu Lys
    370                 375                 380

Gly Asn Leu Ala Ser Glu Gly Ala Val Ala Lys Ile Ser Gly Val Lys
385                 390                 395                 400

Asn Pro Gln Ile Thr Gly Pro Ala Arg Val Phe Asp Ser Glu Glu Ala
                405                 410                 415

Cys Leu Asp Ala Ile Leu Ala Gly Lys Ile Asn Pro Gly Asp Val Ile
            420                 425                 430

Val Ile Arg Tyr Glu Gly Pro Val Gly Gly Pro Gly Met Arg Glu Met
        435                 440                 445

Leu Ala Pro Thr Ser Ala Ile Ile Gly Ala Gly Leu Gly Asp Ser Val
    450                 455                 460

Gly Leu Ile Thr Asp Gly Arg Phe Ser Gly Thr Tyr Gly Met Val
465                 470                 475                 480

Val Gly His Val Ala Pro Glu Ala Ala Val Gly Gly Thr Ile Ala Leu
                485                 490                 495

Val Gln Glu Gly Asp Ser Ile Thr Ile Asp Ala His Arg Arg Leu Leu
            500                 505                 510

Gln Leu Asn Val Ser Glu Glu Leu Ala Ala Arg Arg Ala Lys Trp
        515                 520                 525

Gln Pro Pro Ala Pro Arg Tyr Thr Arg Gly Val Leu Ala Lys Tyr Ala
    530                 535                 540

Lys Leu Val Ser Ser Ser Ser Leu Gly Ala Val Thr Asp Arg Phe Val
545                 550                 555                 560
```

<210> SEQ ID NO 3
<211> LENGTH: 326
<212> TYPE: PRT
<213> ORGANISM: Unknown
<220> FEATURE:
<223> OTHER INFORMATION: Geobacillus stearothermophilus

<400> SEQUENCE: 3

```
Met Thr Thr Asp Leu Phe Thr Ala Leu Lys Ala Lys Val Thr Gly Thr
1               5                   10                  15

Ala Arg Lys Ile Val Phe Pro Glu Gly Thr Asp Asp Arg Ile Leu Thr
            20                  25                  30

Ala Ala Ser Arg Leu Ala Thr Glu Gln Val Leu Gln Pro Ile Val Leu
        35                  40                  45
```

Gly Asp Glu Gln Ala Ile Arg Val Lys Ala Ala Leu Gly Leu Pro
            50                  55                  60

Leu Glu Gly Val Glu Ile Val Asn Pro Arg Tyr Gly Gly Phe Asp
 65                  70                  75                  80

Glu Leu Val Ser Ala Phe Val Glu Arg Lys Gly Lys Val Thr Glu
                85                  90                  95

Glu Thr Ala Arg Glu Leu Leu Phe Asp Glu Asn Tyr Phe Gly Thr Met
            100                 105                 110

Leu Val Tyr Met Gly Ala Ala Asp Gly Leu Val Ser Gly Ala Ala His
            115                 120                 125

Ser Thr Ala Asp Thr Val Arg Pro Ala Leu Gln Ile Ile Lys Thr Lys
            130                 135                 140

Pro Gly Val Asp Lys Thr Ser Gly Val Phe Ile Met Val Arg Gly Asp
145                 150                 155                 160

Glu Lys Tyr Val Phe Ala Asp Cys Ala Ile Asn Ile Ala Pro Asn Ser
                165                 170                 175

His Asp Leu Ala Glu Ile Ala Val Glu Ser Ala Arg Thr Ala Lys Met
            180                 185                 190

Phe Gly Leu Lys Pro Arg Val Val Leu Leu Ser Phe Ser Thr Lys Gly
            195                 200                 205

Ser Ala Ser Ser Pro Glu Thr Glu Lys Val Val Glu Ala Val Arg Leu
210                 215                 220

Ala Lys Glu Met Ala Pro Asp Leu Ile Leu Asp Gly Glu Phe Gln Phe
225                 230                 235                 240

Asp Ala Ala Phe Val Pro Glu Val Ala Lys Lys Ala Pro Asp Ser
                245                 250                 255

Val Ile Gln Gly Asp Ala Asn Val Phe Ile Phe Pro Ser Leu Glu Ala
            260                 265                 270

Gly Asn Ile Gly Tyr Lys Ile Ala Gln Arg Leu Gly Gly Phe Glu Ala
            275                 280                 285

Val Gly Pro Ile Leu Gln Gly Leu Asn Lys Pro Val Asn Asp Leu Ser
            290                 295                 300

Arg Gly Cys Ser Ala Glu Asp Ala Tyr Lys Leu Ala Leu Ile Thr Ala
305                 310                 315                 320

Ala Gln Ser Leu Gly Glu
                325

<210> SEQ ID NO 4
<211> LENGTH: 393
<212> TYPE: PRT
<213> ORGANISM: Unknown
<220> FEATURE:
<223> OTHER INFORMATION: Multispecies Cupriavidus

<400> SEQUENCE: 4

Met Thr Asp Val Val Ile Val Ser Ala Ala Arg Thr Ala Val Gly Lys
 1               5                  10                  15

Phe Gly Gly Ser Leu Ala Lys Ile Pro Ala Pro Glu Leu Gly Ala Val
                20                  25                  30

Val Ile Lys Ala Ala Leu Glu Arg Ala Gly Val Lys Pro Glu Gln Val
            35                  40                  45

Ser Glu Val Ile Met Gly Gln Val Leu Thr Ala Gly Ser Gly Gln Asn
            50                  55                  60

Pro Ala Arg Gln Ala Ala Ile Lys Ala Gly Leu Pro Ala Met Val Pro
 65                  70                  75                  80

Ala Met Thr Ile Asn Lys Val Cys Gly Ser Gly Leu Lys Ala Val Met
            85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Thr Met Ile
130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
            165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
            245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
            275                 280                 285

Met Gly Met Gly Pro Val Pro Ala Ser Lys Arg Ala Leu Ser Arg Ala
            290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
            325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
            355                 360                 365

Arg Asp Ala Lys Lys Gly Leu Ala Ser Leu Cys Ile Gly Gly Gly Met
370                 375                 380

Gly Val Ala Leu Ala Val Glu Arg Lys
385                 390

<210> SEQ ID NO 5
<211> LENGTH: 383
<212> TYPE: PRT
<213> ORGANISM: Enterococcus faecalis

<400> SEQUENCE: 5

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
            35                  40                  45

Gln Asp Ile Val Thr Phe Ala Ala Asn Ala Ala Glu Ala Ile Leu Thr

```
            50                  55                  60
Lys Glu Asp Lys Glu Ala Ile Asp Met Val Ile Val Gly Thr Glu Ser
 65                  70                  75                  80

Ser Ile Asp Glu Ser Lys Ala Ala Val Val Leu His Arg Leu Met
                     85                  90                  95

Gly Ile Gln Pro Phe Ala Arg Ser Phe Glu Ile Lys Glu Gly Cys Tyr
                    100                 105                 110

Gly Ala Thr Ala Gly Leu Gln Leu Ala Lys Asn His Val Ala Leu His
                115                 120                 125

Pro Asp Lys Lys Val Leu Val Val Ala Ala Asp Ile Ala Lys Tyr Gly
130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
                180                 185                 190

Tyr Pro Met Val Asp Gly Pro Leu Ser Asn Glu Thr Tyr Ile Gln Ser
                195                 200                 205

Phe Ala Gln Val Trp Asp Glu His Lys Lys Arg Thr Gly Leu Asp Phe
210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
                260                 265                 270

Val Gly Asn Leu Tyr Thr Ser Ser Leu Tyr Leu Gly Leu Ile Ser Leu
                275                 280                 285

Leu Glu Asn Ala Thr Thr Leu Thr Ala Gly Asn Gln Ile Gly Leu Phe
                290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
                340                 345                 350

Glu Thr Leu Asp Thr Asp Ile Asp Gln Thr Leu Glu Asp Glu Leu Lys
                355                 360                 365

Tyr Ser Ile Ser Ala Ile Asn Asn Thr Val Arg Ser Tyr Arg Asn
                370                 375                 380

<210> SEQ ID NO 6
<211> LENGTH: 803
<212> TYPE: PRT
<213> ORGANISM: Enterococcus faecalis

<400> SEQUENCE: 6

Met Lys Thr Val Val Ile Ile Asp Ala Leu Arg Thr Pro Ile Gly Lys
 1               5                  10                  15

Tyr Lys Gly Ser Leu Ser Gln Val Ser Ala Val Asp Leu Gly Thr His
                20                  25                  30

Val Thr Thr Gln Leu Leu Lys Arg His Ser Thr Ile Ser Glu Glu Ile
                35                  40                  45
```

-continued

```
Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
            115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
            195                 200                 205

Lys Asp Glu Gly Ile Arg Pro Asn Ser Ser Val Glu Lys Leu Gly Thr
    210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
                245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
            275                 280                 285

Ala Ile Gln Lys Leu Leu Ala Arg Asn Gln Leu Thr Thr Glu Glu Ile
    290                 295                 300

Asp Leu Tyr Glu Ile Asn Glu Ala Phe Ala Ala Thr Ser Ile Val Val
305                 310                 315                 320

Gln Arg Glu Leu Ala Leu Pro Glu Glu Lys Val Asn Ile Tyr Gly Gly
                325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Tyr Gly Val
            355                 360                 365

Ala Ser Leu Cys Ile Gly Gly Gly Leu Gly Leu Ala Met Leu Leu Glu
    370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
                405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Val Pro Met Gly Val Gly
            435                 440                 445

Leu His Leu Thr Val Asp Glu Thr Asp Tyr Leu Val Pro Met Ala Thr
    450                 455                 460

Glu Glu Pro Ser Val Ile Ala Ala Leu Ser Asn Gly Ala Lys Ile Ala
```

```
            465                 470                 475                 480
Gln Gly Phe Lys Thr Val Asn Gln Gln Arg Leu Met Arg Gly Gln Ile
                485                 490                 495

Val Phe Tyr Asp Val Ala Asp Ala Glu Ser Leu Ile Asp Glu Leu Gln
            500                 505                 510

Val Arg Glu Thr Glu Ile Phe Gln Gln Ala Glu Leu Ser Tyr Pro Ser
            515                 520                 525

Ile Val Lys Arg Gly Gly Leu Arg Asp Leu Gln Tyr Arg Ala Phe
            530                 535                 540

Asp Glu Ser Phe Ile Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
            595                 600                 605

Ser Arg Leu Ser Lys Gly Ser Asn Gly Arg Glu Ile Ala Glu Lys Ile
            610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
            675                 680                 685

Gln Leu Ile Gly Glu Ile Ser Val Pro Leu Ala Leu Ala Thr Val Gly
            690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
            725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
            755                 760                 765

Gly Ala Thr Gly Lys Glu Val Glu Ala Val Ala Gln Gln Leu Lys Arg
            770                 775                 780

Gln Lys Thr Met Asn Gln Asp Arg Ala Leu Ala Ile Leu Asn Asp Leu
785                 790                 795                 800

Arg Lys Gln

<210> SEQ ID NO 7
<211> LENGTH: 315
<212> TYPE: PRT
<213> ORGANISM: Unknown
<220> FEATURE:
<223> OTHER INFORMATION: Methanosarcina mazei

<400> SEQUENCE: 7

Met Leu Lys Phe Ser Lys Ile Glu Lys Leu Leu Arg Asn Asn Met Val
1               5                   10                  15

Ser Cys Ser Ala Pro Gly Lys Ile Tyr Leu Phe Gly Glu His Ala Val
            20                  25                  30
```

Val Tyr Gly Glu Thr Ala Ile Ala Cys Ala Val Glu Leu Arg Thr Arg
        35                  40                  45

Val Arg Ala Glu Leu Asn Asp Ser Ile Thr Ile Gln Ser Gln Ile Gly
 50                  55                  60

Arg Thr Gly Leu Asp Phe Glu Lys His Pro Tyr Val Ser Ala Val Ile
 65                  70                  75                  80

Glu Lys Met Arg Lys Ser Ile Pro Ile Asn Gly Val Phe Leu Thr Val
                 85                  90                  95

Asp Ser Asp Ile Pro Val Gly Ser Gly Leu Gly Ser Ser Ala Ala Val
                100                 105                 110

Thr Ile Ala Ser Ile Gly Ala Leu Asn Glu Leu Phe Gly Phe Gly Leu
                115                 120                 125

Ser Leu Gln Glu Ile Ala Lys Leu Gly His Glu Ile Glu Ile Lys Val
                130                 135                 140

Gln Gly Ala Ala Ser Pro Thr Asp Thr Tyr Val Ser Thr Phe Gly Gly
145                 150                 155                 160

Val Val Thr Ile Pro Glu Arg Arg Lys Leu Lys Thr Pro Asp Cys Gly
                165                 170                 175

Ile Val Ile Gly Asp Thr Gly Val Phe Ser Ser Thr Lys Glu Leu Val
                180                 185                 190

Ala Asn Val Arg Gln Leu Arg Glu Ser Tyr Pro Asp Leu Ile Glu Pro
                195                 200                 205

Leu Met Thr Ser Ile Gly Lys Ile Ser Arg Ile Gly Glu Gln Leu Val
                210                 215                 220

Leu Ser Gly Asp Tyr Ala Ser Ile Gly Arg Leu Met Asn Val Asn Gln
225                 230                 235                 240

Gly Leu Leu Asp Ala Leu Gly Val Asn Ile Leu Glu Leu Ser Gln Leu
                245                 250                 255

Ile Tyr Ser Ala Arg Ala Ala Gly Ala Phe Gly Ala Lys Ile Thr Gly
                260                 265                 270

Ala Gly Gly Gly Gly Cys Met Val Ala Leu Thr Ala Pro Glu Lys Cys
                275                 280                 285

Asn Gln Val Ala Glu Ala Ile Ala Gly Ala Gly Gly Lys Val Thr Ile
                290                 295                 300

Thr Lys Pro Thr Glu Gln Gly Leu Lys Val Asp
305                 310                 315

<210> SEQ ID NO 8
<211> LENGTH: 335
<212> TYPE: PRT
<213> ORGANISM: Streptococcus pneumoniae

<400> SEQUENCE: 8

Met Ile Ala Val Lys Thr Cys Gly Lys Leu Tyr Trp Ala Gly Glu Tyr
 1               5                  10                  15

Ala Ile Leu Glu Pro Gly Gln Leu Ala Leu Ile Lys Asp Ile Pro Ile
                20                  25                  30

Tyr Met Arg Ala Glu Ile Ala Phe Ser Asp Ser Tyr Arg Ile Tyr Ser
                35                  40                  45

Asp Met Phe Asp Phe Ala Val Asp Leu Arg Pro Asn Pro Asp Tyr Ser
                50                  55                  60

Leu Ile Gln Glu Thr Ile Ala Leu Met Gly Asp Phe Leu Ala Val Arg
 65                  70                  75                  80

Gly Gln Asn Leu Arg Pro Phe Ser Leu Ala Ile Tyr Gly Lys Met Glu

```
                    85                  90                  95
Arg Glu Gly Lys Lys Phe Gly Leu Gly Ser Ser Gly Ser Val Val
                100                 105                 110

Leu Val Val Lys Ala Leu Leu Ala Leu Tyr Asn Leu Ser Val Asp Gln
            115                 120                 125

Asn Leu Leu Phe Lys Leu Thr Ser Ala Val Leu Leu Lys Arg Gly Asp
        130                 135                 140

Asn Gly Ser Met Gly Asp Leu Ala Cys Ile Ala Ala Glu Asp Leu Val
145                 150                 155                 160

Leu Tyr Gln Ser Phe Asp Arg Gln Lys Val Ala Ala Trp Leu Glu Glu
                165                 170                 175

Glu Asn Leu Ala Thr Val Leu Glu Arg Asp Trp Gly Phe Ser Ile Ser
            180                 185                 190

Gln Val Lys Pro Thr Leu Glu Cys Asp Phe Leu Val Gly Trp Thr Lys
        195                 200                 205

Glu Val Ala Val Ser Ser His Met Val Gln Gln Ile Lys Gln Asn Ile
210                 215                 220

Asn Gln Asn Phe Leu Thr Ser Ser Lys Glu Thr Val Val Ser Leu Val
225                 230                 235                 240

Glu Ala Leu Glu Gln Gly Lys Ser Glu Lys Ile Ile Glu Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Ala Val Ala
        275                 280                 285

Lys Ser Ser Gly Ala Gly Gly Asp Cys Gly Ile Ala Leu Ser Phe
290                 295                 300

Asp Ala Gln Ser Thr Lys Thr Leu Lys Asn Arg Trp Ala Asp Leu Gly
305                 310                 315                 320

Ile Glu Leu Leu Tyr Gln Glu Arg Ile Gly His Asp Asp Lys Ser
                325                 330                 335

<210> SEQ ID NO 9
<211> LENGTH: 344
<212> TYPE: PRT
<213> ORGANISM: Streptococcus pneumoniae

<400> SEQUENCE: 9

Met Tyr His Ser Leu Gly Asn Gln Phe Asp Thr Arg Thr Arg Thr Ser
1               5                   10                  15

Arg Lys Ile Arg Arg Glu Arg Ser Cys Ser Asp Met Asp Arg Glu Pro
            20                  25                  30

Val Thr Val Arg Ser Tyr Ala Asn Ile Ala Ile Lys Tyr Trp Gly
        35                  40                  45

Lys Lys Lys Glu Lys Glu Met Val Pro Ala Thr Ser Ser Ile Ser Leu
    50                  55                  60

Thr Leu Glu Asn Met Tyr Thr Glu Thr Thr Leu Ser Pro Leu Pro Ala
65                  70                  75                  80

Asn Val Thr Ala Asp Glu Phe Tyr Ile Asn Gly Gln Leu Gln Asn Glu
                85                  90                  95

Val Glu His Ala Lys Met Ser Lys Ile Ile Asp Arg Tyr Arg Pro Ala
            100                 105                 110

Gly Glu Gly Phe Val Arg Ile Asp Thr Gln Asn Asn Met Pro Thr Ala
        115                 120                 125
```

```
Ala Gly Leu Ser Ser Ser Ser Gly Leu Ser Ala Leu Val Lys Ala
    130                 135                 140

Cys Asn Ala Tyr Phe Lys Leu Gly Leu Asp Arg Ser Gln Leu Ala Gln
145                 150                 155                 160

Glu Ala Lys Phe Ala Ser Gly Ser Ser Arg Ser Phe Tyr Gly Pro
                165                 170                 175

Leu Gly Ala Trp Asp Lys Asp Ser Gly Glu Ile Tyr Pro Val Glu Thr
                180                 185                 190

Asp Leu Lys Leu Ala Met Ile Met Leu Val Leu Glu Asp Lys Lys
            195                 200                 205

Pro Ile Ser Ser Arg Asp Gly Met Lys Leu Cys Val Glu Thr Ser Thr
    210                 215                 220

Thr Phe Asp Asp Trp Val Arg Gln Ser Glu Lys Asp Tyr Gln Asp Met
225                 230                 235                 240

Leu Ile Tyr Leu Lys Glu Asn Asp Phe Ala Lys Ile Gly Glu Leu Thr
                245                 250                 255

Glu Lys Asn Ala Leu Ala Met His Ala Thr Thr Lys Thr Ala Ser Pro
            260                 265                 270

Ala Phe Ser Tyr Leu Thr Asp Ala Ser Tyr Glu Ala Met Asp Phe Val
    275                 280                 285

Arg Gln Leu Arg Glu Lys Gly Glu Ala Cys Tyr Phe Thr Met Asp Ala
    290                 295                 300

Gly Pro Asn Val Lys Val Phe Cys Gln Glu Lys Asp Leu Glu His Leu
305                 310                 315                 320

Ser Glu Ile Phe Gly Gln Arg Tyr Arg Leu Ile Val Ser Lys Thr Lys
                325                 330                 335

Asp Leu Ser Gln Asp Asp Cys Cys
            340

<210> SEQ ID NO 10
<211> LENGTH: 182
<212> TYPE: PRT
<213> ORGANISM: Unknown
<220> FEATURE:
<223> OTHER INFORMATION: Multispecies Bacteria

<400> SEQUENCE: 10

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
                20                  25                  30

Leu Ala Phe Ser Ser Trp Leu Phe Asn Ala Lys Gly Gln Leu Leu Val
            35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
                100                 105                 110

Val Glu Asn Glu Val Cys Pro Val Phe Ala Ala Arg Thr Thr Ser Ala
            115                 120                 125

Leu Gln Ile Asn Asp Asp Glu Val Met Asp Tyr Gln Trp Cys Asp Leu
    130                 135                 140
```

```
Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 11
<211> LENGTH: 297
<212> TYPE: PRT
<213> ORGANISM: Unknown
<220> FEATURE:
<223> OTHER INFORMATION: Geobacillus stearothermophilus

<400> SEQUENCE: 11

Met Ala Gln Leu Ser Val Glu Gln Phe Leu Asn Glu Gln Lys Gln Ala
1               5                   10                  15

Val Glu Thr Ala Leu Ser Arg Tyr Ile Glu Arg Leu Glu Gly Pro Ala
                20                  25                  30

Lys Leu Lys Lys Ala Met Ala Tyr Ser Leu Glu Ala Gly Gly Lys Arg
            35                  40                  45

Ile Arg Pro Leu Leu Leu Ser Thr Val Arg Ala Leu Gly Lys Asp
        50                  55                  60

Pro Ala Val Gly Leu Pro Val Ala Cys Ala Ile Glu Met Ile His Thr
65                  70                  75                  80

Tyr Phe Leu Ile His Asp Asp Leu Pro Ser Met Asp Asn Asp Asp Leu
                85                  90                  95

Arg Arg Gly Lys Pro Thr Asn His Lys Val Phe Gly Glu Ala Met Ala
            100                 105                 110

Ile Leu Ala Gly Asp Gly Leu Leu Thr Tyr Ala Phe Gln Leu Ile Thr
        115                 120                 125

Glu Ile Asp Asp Glu Arg Ile Pro Pro Ser Val Arg Leu Arg Leu Ile
130                 135                 140

Glu Arg Leu Ala Lys Ala Ala Gly Pro Glu Gly Met Val Ala Gly Gln
145                 150                 155                 160

Ala Ala Asp Met Glu Gly Glu Gly Lys Thr Leu Thr Leu Ser Glu Leu
                165                 170                 175

Glu Tyr Ile His Arg His Lys Thr Gly Lys Met Leu Gln Tyr Ser Val
            180                 185                 190

His Ala Gly Ala Leu Ile Gly Gly Ala Asp Ala Arg Gln Thr Arg Glu
        195                 200                 205

Leu Asp Glu Phe Ala Ala His Leu Gly Leu Ala Phe Gln Ile Arg Asp
210                 215                 220

Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
                245                 250                 255

Leu Ala Gly Ala Lys Glu Lys Leu Ala Phe His Ile Glu Ala Ala Gln
            260                 265                 270

Arg His Leu Arg Asn Ala Asp Val Asp Gly Ala Ala Leu Ala Tyr Ile
        275                 280                 285

Cys Glu Leu Val Ala Ala Arg Asp His
290                 295

<210> SEQ ID NO 12
<211> LENGTH: 300
```

```
<212> TYPE: PRT
<213> ORGANISM: Unknown
<220> FEATURE:
<223> OTHER INFORMATION: Rhizobacteria

<400> SEQUENCE: 12

Met Ala Leu Asp Glu Ala Pro Ala Glu Arg Pro Gly Ser Arg Ala
1               5                   10                  15

Val Glu Leu Glu Ile Asp Gly Arg Ser Arg Ile Phe Asp Ile Asp
                20                  25                  30

Pro Asp Leu Pro Lys Trp Ile Asp Glu Ala Phe Arg Ser Asp Asp
                35                  40                  45

Tyr Pro Tyr Lys Lys Leu Asp Arg Glu Glu Tyr Glu Glu Thr Leu
50                      55                  60

Thr Lys Leu Gln Ile Glu Leu Val Lys Val Gln Phe Trp Met Gln Ala
65                  70                  75                  80

Thr Gly Lys Arg Val Met Ala Val Phe Glu Gly Arg Asp Ala Ala Gly
                    85                  90                  95

Lys Gly Gly Ala Ile His Ala Thr Thr Ala Asn Met Asn Pro Arg Ser
                100                 105                 110

Ala Arg Val Val Ala Leu Thr Lys Pro Thr Glu Thr Glu Arg Gly Gln
                115                 120                 125

Trp Tyr Phe Gln Arg Tyr Val Ala Thr Phe Pro Thr Ala Gly Glu Phe
130                 135                 140

Val Leu Phe Asp Arg Ser Trp Tyr Asn Arg Ala Gly Val Glu Pro Val
145                 150                 155                 160

Met Gly Phe Cys Thr Pro Asp Gln Tyr Glu Gln Phe Leu Lys Glu Ala
                165                 170                 175

Pro Arg Phe Glu Glu Met Ile Ala Asn Glu Gly Ile His Leu Phe Lys
                180                 185                 190

Phe Trp Ile Asn Ile Gly Arg Glu Met Gln Leu Lys Arg Phe His Asp
                195                 200                 205

Arg Arg His Asp Pro Leu Lys Ile Trp Lys Leu Ser Pro Met Asp Ile
210                 215                 220

Ala Ala Leu Ser Lys Trp Asp Asp Tyr Thr Gly Lys Arg Asp Arg Met
225                 230                 235                 240

Leu Lys Glu Thr His Thr Glu His Gly Pro Trp Ala Val Ile Arg Gly
                245                 250                 255

Asn Asp Lys Arg Arg Ser Arg Ile Asn Val Ile Arg His Met Leu Thr
                260                 265                 270

Lys Leu Asp Tyr Asp Gly Lys Asp Glu Ala Ala Ile Gly Glu Val Asp
                275                 280                 285

Glu Lys Ile Leu Gly Ser Gly Pro Gly Phe Leu Arg
290                 295                 300

<210> SEQ ID NO 13
<211> LENGTH: 261
<212> TYPE: PRT
<213> ORGANISM: Unknown
<220> FEATURE:
<223> OTHER INFORMATION: Bacillus sp. G3

<400> SEQUENCE: 13

Met Tyr Ser Asp Leu Glu Gly Lys Val Val Ile Thr Gly Ser Ala
1               5                   10                  15

Ser Gly Leu Gly Arg Ala Met Gly Val Arg Phe Ala Arg Glu Lys Ala
                20                  25                  30
```

```
Lys Val Val Ile Asn Tyr Arg Ser Arg Glu Ser Glu Ala Asn Asp Val
        35                  40                  45
Leu Glu Glu Ile Lys Lys Val Gly Gly Glu Ala Ile Ala Val Lys Gly
    50                  55                  60
Asp Val Thr Val Glu Ser Asp Val Val Asn Leu Ile Gln Ser Ala Val
65                  70                  75                  80
Lys Glu Phe Gly Thr Leu Asp Val Met Ile Asn Asn Ala Gly Ile Glu
                85                  90                  95
Asn Ala Val Pro Ser His Glu Met Pro Leu Glu Asp Trp Asn Arg Val
            100                 105                 110
Ile Asn Thr Asn Leu Thr Gly Ala Phe Leu Gly Ser Arg Glu Ala Ile
        115                 120                 125
Lys Tyr Phe Val Glu His Asp Ile Lys Gly Ser Val Ile Asn Met Ser
    130                 135                 140
Ser Val His Glu Lys Ile Pro Trp Pro Leu Phe Val His Tyr Ala Ala
145                 150                 155                 160
Ser Lys Gly Gly Met Lys Leu Met Thr Glu Thr Leu Ala Met Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Lys Arg Ala Asp
        195                 200                 205
Val Glu Ser Met Ile Pro Met Gly Tyr Ile Gly Lys Pro Glu Glu Ile
    210                 215                 220
Ala Ala Val Ala Thr Trp Leu Ala Ser Ser Glu Ala Ser Tyr Val Thr
225                 230                 235                 240
Gly Ile Thr Leu Phe Ala Asp Gly Gly Met Thr Leu Tyr Pro Ser Phe
                245                 250                 255
Gln Ala Gly Arg Gly
                260
```